(12) United States Patent
Bystron et al.

(10) Patent No.: US 9,086,422 B2
(45) Date of Patent: Jul. 21, 2015

(54) CHROMATOGRAPHY SYSTEMS AND SYSTEM COMPONENTS

(75) Inventors: Josef Bystron, Chicago, IL (US); Dirk Helgemo, Shakopee, MN (US); James Anderson, Jr., Arlington Heights, IL (US); Washington Mendoza, Lake in the Hills, IL (US); Raaidah Saari-Nordhaus, Antioch, IL (US); Steve Lewis, Bloomington, MN (US); Sheldon Nelson, Plymouth, MN (US); Bruce Frohman, St. Louis Park, MN (US); Nick Klein, Coon Rapids, MN (US)

(73) Assignee: Alltech Associates, Inc., Columbia, MD (US)

( * ) Notice: Subject to any disclaimer, the term of this patent is extended or adjusted under 35 U.S.C. 154(b) by 1006 days.

(21) Appl. No.: 13/139,016

(22) PCT Filed: Dec. 10, 2009

(86) PCT No.: PCT/US2009/006497
§ 371 (c)(1),
(2), (4) Date: Mar. 27, 2012

(87) PCT Pub. No.: WO2010/068276
PCT Pub. Date: Jun. 17, 2010

(65) Prior Publication Data
US 2012/0175289 A1 Jul. 12, 2012

Related U.S. Application Data

(60) Provisional application No. 61/201,350, filed on Dec. 10, 2008.

(51) Int. Cl.
*B01D 15/08* (2006.01)
*B01D 15/10* (2006.01)
(Continued)

(52) U.S. Cl.
CPC .............. *G01N 30/82* (2013.01); *B01D 15/10* (2013.01); *G01N 30/6091* (2013.01);
(Continued)

(58) Field of Classification Search
CPC ...... B01D 15/08; B01D 15/10; B01D 15/247; B01D 15/02; G01N 30/02; G01N 30/80; G01N 30/82; G01N 35/00732; G01N 35/6091; G01N 35/00782; G01N 35/00792; G01N 2035/00821; G01N 2035/00831; G01N 30/041; G01N 30/6091; G01N 30/8651; G01N 30/8655; G01N 2035/00732; G01N 2035/00782; G01N 2035/00792; G01N 2035/00801; G01N 2035/00811; G01N 2035/041; G01B 21/16
USPC ............... 210/85, 91, 94, 143, 198.2; 422/70, 422/82.05; 73/61.52–61.58; 340/10.51
See application file for complete search history.

(56) References Cited

U.S. PATENT DOCUMENTS 3,694,085 A 9/1972 Rich ................................ 356/37
3,700,333 A 10/1972 Charleson et al. ............ 356/103
(Continued)

FOREIGN PATENT DOCUMENTS

EP 1380329 1/2004 ............. B01D 15/08
EP 1370571 6/2005 ............... C07K 1/36
(Continued)

OTHER PUBLICATIONS

U.S. Appl. No. 12/959,933, filed Nov. 3, 2010, Anderson, James et al.
(Continued)

Primary Examiner — Joseph Drodge
(74) Attorney, Agent, or Firm — Beverly J. Artale

(57) ABSTRACT

Chromatography systems and components suitable for use in chromatography systems are disclosed. Methods of making chromatography systems and components suitable for use in chromatography systems and methods of using chromatography systems and components suitable for use in chromatography systems are also disclosed.

28 Claims, 6 Drawing Sheets

(51) Int. Cl.
| | |
|---|---|
| *G01N 35/10* | (2006.01) |
| *G01N 30/30* | (2006.01) |
| *G01N 30/82* | (2006.01) |
| *G01N 30/60* | (2006.01) |
| *G01N 35/00* | (2006.01) |
| *B01D 15/24* | (2006.01) |
| *G01N 35/04* | (2006.01) |

(52) U.S. Cl.
CPC ......... *G01N 35/00732* (2013.01); *B01D 15/08* (2013.01); *B01D 15/247* (2013.01); *G01N 2035/00782* (2013.01); *G01N 2035/00811* (2013.01); *G01N 2035/041* (2013.01)

(56) References Cited

U.S. PATENT DOCUMENTS

| | | | |
|---|---|---|---|
| 3,738,751 A | 6/1973 | Rich | 356/37 |
| 3,787,123 A | 1/1974 | Sigrist | 356/103 |
| 3,806,248 A | 4/1974 | Sinclair | 356/37 |
| 3,975,946 A | 8/1976 | Ball et al. | 73/61.1 |
| 4,066,411 A | 1/1978 | Fine et al. | 23/253 |
| 4,112,297 A | 9/1978 | Miyagi et al. | 250/288 |
| 4,293,217 A | 10/1981 | Bird, Jr. et al. | 356/37 |
| 4,357,420 A | 11/1982 | Bostick et al. | 435/8 |
| 4,565,446 A | 1/1986 | Chu | 356/246 |
| 4,622,457 A | 11/1986 | Bradley et al. | 235/464 |
| 4,748,377 A | 5/1988 | King | 315/3.5 |
| 4,775,481 A | 10/1988 | Allington | 210/656 |
| 4,883,958 A | 11/1989 | Vestal | 250/288 |
| 4,894,529 A | 1/1990 | Borden et al. | 250/222.2 |
| 4,940,327 A | 7/1990 | Lilienfeld | 356/338 |
| 4,958,529 A | 9/1990 | Vestal | 73/864.81 |
| 5,030,002 A | 7/1991 | North, Jr. | 356/73 |
| 5,033,541 A | 7/1991 | D'Silva | 165/155 |
| 5,227,135 A | 7/1993 | Godec et al. | 422/98 |
| 5,234,586 A | 8/1993 | Afeyan et al. | 210/198.2 |
| 5,306,426 A | 4/1994 | Afeyan | 210/635 |
| 5,495,108 A | 2/1996 | Apffel et al. | 250/288 |
| 5,538,643 A | 7/1996 | Kallos et al. | 210/656 |
| 5,814,128 A | 9/1998 | Jiang et al. | 95/82 |
| 6,106,710 A | 8/2000 | Fischer et al. | 210/198.2 |
| RE36,892 E | 10/2000 | Apffel, Jr. et al. | 250/288 |
| 6,183,635 B1 | 2/2001 | Klee et al. | 210/198.2 |
| 6,229,605 B1 | 5/2001 | Benedict | 356/339 |
| 6,289,914 B1 | 9/2001 | Tommasi | 137/15.18 |
| 6,294,087 B1 | 9/2001 | Hargro et al. | 210/198.2 |
| 6,362,880 B1 | 3/2002 | Anderson, Jr. et al. | 356/337 |
| 6,377,341 B1 | 4/2002 | Rowlen et al. | 356/128 |
| 6,406,633 B1 | 6/2002 | Fischer et al. | 210/659 |
| 6,436,292 B1 | 8/2002 | Petro | 210/656 |
| 6,461,515 B1 | 10/2002 | Safir et al. | 210/656 |
| 6,568,245 B2 | 5/2003 | Kaufman | 73/28.02 |
| 6,627,075 B1 | 9/2003 | Weissgerber et al. | 210/198.2 |
| 6,707,035 B2 | 3/2004 | Hughey et al. | 250/288 |
| 6,712,085 B2 | 3/2004 | Weissgerber et al. | 137/12 |
| 6,730,228 B2 | 5/2004 | Petro et al. | 210/656 |
| 6,767,467 B2 | 7/2004 | Fischer et al. | 210/659 |
| 6,776,902 B2 | 8/2004 | Petro | 210/198.2 |
| 6,855,258 B2 | 2/2005 | Petro et al. | 210/656 |
| 6,867,415 B2 | 3/2005 | Hughey et al. | 250/288 |
| 6,890,489 B2 | 5/2005 | Nichols et al. | 422/103 |
| 6,984,524 B2 | 1/2006 | Nguyen et al. | 436/107 |
| 6,989,129 B2 | 1/2006 | Licklider et al. | 422/70 |
| 7,006,218 B2 | 2/2006 | Anderson, Jr. et al. | 356/337 |
| 7,129,479 B2 | 10/2006 | Carroll et al. | 250/287 |
| 7,169,308 B2 | 1/2007 | Ohkura | 210/656 |
| 7,214,320 B1 | 5/2007 | Gregori et al. | 210/656 |
| 7,267,796 B2 | 9/2007 | Waki | 422/70 |
| 7,275,682 B2 * | 10/2007 | Excoffier et al. | 235/375 |
| 7,290,723 B1 | 11/2007 | Lu et al. | 239/135 |
| 7,318,900 B2 | 1/2008 | DeMarco | 210/656 |
| 7,419,598 B2 | 9/2008 | Davison | 201/656 |
| 7,429,731 B1 | 9/2008 | Karpetsky | 250/288 |
| 7,575,723 B2 | 8/2009 | Nichols et al. | 422/103 |
| 7,686,959 B2 | 3/2010 | Horsman et al. | 210/656 |
| 7,901,628 B2 | 3/2011 | Yamamoto | 422/70 |
| 2001/0013494 A1 | 8/2001 | Maiefski et al. | 210/656 |
| 2001/0038071 A1 | 11/2001 | Nichols et al. | 250/288 |
| 2002/0121468 A1 | 9/2002 | Fischer et al. | 210/198.2 |
| 2002/0146349 A1 | 10/2002 | Gygi et al. | 422/70 |
| 2002/0190001 A1 | 12/2002 | Petro | 210/656 |
| 2003/0080062 A1 | 5/2003 | Petro et al. | 210/656 |
| 2003/0089663 A1 | 5/2003 | Petro et al. | 210/656 |
| 2003/0224390 A1 | 12/2003 | Fowlkes et al. | 435/6 |
| 2005/0175683 A1 | 8/2005 | Zhang | 424/450 |
| 2005/0226778 A1 | 10/2005 | Houser et al. | 422/99 |
| 2005/0239152 A1 | 10/2005 | Irth et al. | 435/8 |
| 2006/0027490 A1* | 2/2006 | DeMarco | 210/198.2 |
| 2006/0075806 A1 | 4/2006 | Gilby et al. | 73/61.57 |
| 2006/0085139 A1 | 4/2006 | Collette et al. | 702/20 |
| 2006/0093521 A1 | 5/2006 | Swartz et al. | 422/70 |
| 2006/0192108 A1 | 8/2006 | Yeatman et al. | 250/288 |
| 2006/0219637 A1 | 10/2006 | Killeen et al. | 210/656 |
| 2006/0238744 A1 | 10/2006 | O'Donohue | 356/37 |
| 2006/0283945 A1 | 12/2006 | Excoffier et al. | 235/439 |
| 2006/0285108 A1 | 12/2006 | Morrisroe | 356/316 |
| 2007/0023037 A1 | 2/2007 | Larsen et al. | 128/200.18 |
| 2007/0056357 A1 | 3/2007 | Ruegenberg et al. | 73/53.01 |
| 2007/0089493 A1 | 4/2007 | Alington et al. | 73/61.52 |
| 2007/0122314 A1 | 5/2007 | Strand et al. | 422/100 |
| 2007/0132229 A1 | 6/2007 | Mueller et al. | 285/124.2 |
| 2007/0181505 A1 | 8/2007 | DeMarco | 210/656 |
| 2007/0291009 A1 | 12/2007 | Wright et al. | 345/173 |
| 2008/0144003 A1 | 6/2008 | Blackford et al. | 356/37 |
| 2008/0164210 A1* | 7/2008 | DeMarco | 210/656 |
| 2008/0186489 A1 | 8/2008 | Ahn | 356/337 |
| 2008/0202927 A1 | 8/2008 | Kayyem et al. | 204/403.01 |
| 2008/0235081 A1* | 9/2008 | Davison et al. | 705/10 |
| 2010/0229635 A1* | 9/2010 | Kerr | 73/61.55 |
| 2010/0238444 A1 | 9/2010 | Anderson et al. | 356/436 |
| 2011/0017670 A1 | 1/2011 | Anderson et al. | 210/656 |

FOREIGN PATENT DOCUMENTS

| | | | |
|---|---|---|---|
| EP | 01707957 | 10/2006 | G01N 30/20 |
| EP | 1348958 | 9/2008 | G01N 30/60 |
| JP | 2008107136 | 5/2008 | G01N 30/02 |
| WO | 9925451 | 5/1999 | B01D 15/08 |
| WO | 9925452 | 5/1999 | B01D 15/08 |
| WO | 0026662 | 5/2000 | G01N 30/22 |
| WO | 0037157 | 6/2000 | B01D 15/08 |
| WO | 0045929 | 8/2000 | B01D 15/08 |
| WO | 0136071 | 5/2001 | B01D 57/02 |
| WO | 02063291 | 8/2002 | G01N 30/00 |
| WO | 02082071 | 10/2002 | G01N 30/08 |
| WO | 03008101 | 1/2003 | B01L 3/00 |
| WO | 03021251 | 3/2003 | G01N 30/88 |
| WO | 2005116628 | 12/2005 | G01N 30/80 |
| WO | 2006042365 | 4/2006 | G01N 30/89 |
| WO | 2008070776 | 6/2008 | G01N 30/62 |
| WO | 2008118808 | 10/2008 | G01N 30/80 |
| WO | 2009075764 | 6/2009 | G01N 30/82 |

OTHER PUBLICATIONS

U.S. Appl. No. 12/960,042, filed Dec. 3, 2010, Anderson, James et al.
U.S. Appl. No. 12/960,114, filed Dec. 3, 2010, Anderson, James et al.
U.S. Appl. No. 13/132,619, filed Jun. 3, 2011, Olsen, Kristine et al.
U.S. Appl. No. 13/133,733, filed Jun. 9, 2011, Anderson, James et al.
U.S. Appl. No. 13/133,837, filed Jun. 9, 2011, Saari-Nordhaus, Raaidah et al.
U.S. Appl. No. 13/139,030, filed Jun. 10, 2011, Bystron Josef, et al.
U.S. Appl. No. 13/139,061, filed Jun. 10, 2011, Saari-Nordhaus, Raaidah.
U.S. Appl. No. 13/262,756, filed Oct. 3, 2011, McCreary Dennis et al.
U.S. Appl. No. 13/266,870, filed Oct. 28, 2011, Saari-Nordhaus, Raaidah et al.
Automated Semipreparative Purification with Mass Spectrometric Fraction Collection Trigger: Modeling and Experimental Evaluation of a Setup Employing Passive Splitting by Steiner, F., Mahsunah A., Arnold F., Piecha T., Huber C.; J. Sep. Sci 2007, 30, 1496-1508.

(56) References Cited

OTHER PUBLICATIONS

Blue Natural Organic Dyestuffs—From Textile Dyeing to Mural Painting. Separation and Characterization of Coloring Matters Present in Elderberry, Logwood and Indigo by Pawlak, K., Puchalska, M., Miszczak, A., Rostoniec, E., and Jarosz, M.,; Journal of Mass Spectrometry 2006; 41: 613-622.
High-Throughput Purification of Combinatorial Libraries I: A High-Throughput Purification System Using an Acclerated Retention Window Approach by Yan, B., Collins, N., Wheatley, J., Irving, M., Leopold, K., Chan, C., Shornikov, A., Fang, L., Lee, A., Stock, M., and Zhao, J.; J. Comb Chem. 2004, 6, 255-261.
Optimal Fraction Collecting in Preparative LC/MS by Rosentreter, U. and Huber, U.; Journal of Combinatorial Chemistry, vol. 6, No. 2.
Purification of Alkaloids from Corydalis Yanhusuo W.T. Wang Using Preparative 2-D HPLC by Zhang, Jing; Jin, Yu; Liu, Yanfang; Xiao, Yuansheng; Feng, Jiatao; Xue, Xingya; Zhang, Xiuli; Liang, Xinmiao; J. Sep. Sci. 2009, 31, 1401-1406.
Quantification of fipronil and its metabolite fipronil sulfone in rat plasma over a wide range of concentrations by LC/UV/MS by Lacroix, M Z; Puel, S; Toutain, P L; Viguioe, C.; J Chromatogr B Analyt Technol Biomed Life Sci vol. 878, No. 22.
Role of mass spectrometry in the purification of peptides and proteins by Mazza, C. B.; Cavanaugh, J. Y.; Neue, U. D.; Phillips, D. J.; J. Chromatogr. B Anal. Technol. Biomed. Life Sci vol. 790.
Sample preparation for hyphenated analytical techniques by Rosenfeld, J.M.; p. 121-123.
Separation and Identification of Compounds in Adinandra Nitida by Comprehensive Two-Dimensional Liquid Chromatography Coupled to Atmospheric Pressure Chemical Ionization Source Ion Trap Tandem Mass Spectrometry by J. Zhang, D. Tao, J. Duan, Z. Liang, W. Zhang, L. Zhang, Y. Huo, and Y. Zhang. From Anal Bioanal Chem (2006) 386: 586-593.
On-Line Sample Enrichment System Coupled to Electrospray Ionization Time-of-Flight Mass Spectrometry (ESI-TOF-MS) by M. Okamoto, K. Yamashita, and K. Nakai from Journal of Pharmaceutical and Biomedical Analysis 41 (2006) 707-713.
Liquid Chromatography with Ultraviolet Absorbance-Mass Spectrometric Detection and with Nuclear Magnetic Resonance Spectroscopy: A Powerful Combination for the On-Line Structural Investigation of Plant Metabolites by J. Wolfender, K Ndjoko, and K Hostettmann from Journal of Chromatography A, 1000 (2003) 437-455.
A Straightforward Means of Coupling Preparative High-Perfromance Liquid Chromatography and Mass Spectrometry by H. Cai, J. Kiplinger, W. Goetzinger, R. Cole, K. Laws, M. Foster, and A Schrock from Rapid Communications in Mass Spectrometry (2002) 16: 544-554.
A novel hyphenated LC-ARC-RD-MS-FC system for identification of drug metabolites; Proceedings of the 50th ASMS Conference on Mass Spectrometry and Allied Topics, Orlando Florida, Jun. 2-6, 2002 by Wenzhe Lu, ChungPing Yu, Dian Y. Lee.
Analysis of Rhubarb by Liquid Chromatography-Electrospray-Mass Spectrometry; Tamkang Journal of Science and Engineering, Vik. 6, No. 1, pp. 31-36 (2003) by Ming-Ren S. Fuh and Hung-Jian Lin.
Automated simultaneous isolation and quantitation of labeled amino acid fractions from plasma and tissue by ion-exchange chromatography; Journal of Chromatography B, 660 (1994) 251-257 by Hans M.H. van Eijik, Mark P.L. Huinck, Dennis R. Rooyakkers, Nicolaas E.P. Deutz.
Characterization of apolipoprotein and apolipoprotein precursors in pancreatic cancer serum samples via two-dimensional liquid chromatography and mass spectrometry; Journal of Chromatography A. 1162 (2007) 117-125 by Jianzhong Chen, Michelle Anderson, David E. Misek, Diane M. Simeone, and David M Lubman.
Evaluation of applicability of the flow splitter to frit-FAB LC-MS system; Mass Spectroscopy vol. 39, No. 4, Aug. 1991 by Yoshitomo Ikai, Hisao Oka, Junko Hayakawa, Ken-ichi Harada, and Makato Suzuki.
High-Throughput Mass-Directed Parallel Purification Incorporating a Multiplexed Single Quadrupole Mass Spectrometer; Anal. Chem. 2002, 74, 3055-3062 by Rongda Xu, Tao Wang, John Isbell, Zhe Cai, Christopher Sykes, Andrew Brailsford, and Daniel B. Kassel.
Hyphenation of centrifugal partition chromatography with electrospray ionization mass spectrometry using an active flow-splitter device for characterization of flavonol glycosides; Rapid Communications in Mass Spectrometry 2009; 23; 1863-1870 by Alix Toribio, Emilie Desandau, Claire Elfakir, and Michel Lafosse.
Hyphenation of high performance liquid chromatography with sector field inductively coupled plasma mass spectrometry for the determination of ultra-trace level anionic and cationic arsenic compounds in freshwater fish; J. Anal. At. Spectrom., 2004, 19, 191-195 by Jian Zheng and Holger Hintelmann.
Identification of intact glucosinolates using direct coupling of high-performance liquid chromatography with continuous-flow frit fast atom bombardment tandem mass spectrometry; Biological Mass Spectrometry, vol. 20, 259-263 (1991) by P.S. Kokkonen, J. van der Greef, W.M.A. Niessen, U.R. Tjaden, G.J. ten Hove, and G. van de Werken.
Improved liquid chromatography—mass spectrometry performance in quantitative analysis using a nanosplitter interface; Journal of Chromatography A. 1053 (2004) 151-159 by Christine L. Andrews, Chung-Ping Yu, Eric Yang, and Paul Vouros.
Novel system for separation of phospholipids by high-performance liquid chromatography; Journal of Chromatography, 234 (1982) 218-221 by Iftekhar Alam, J. Bryan Smith, Melvin J. Silver, and David Ahern.
Optimization of a liquid chromatography method based on simulataneous electrospray ionization mass spectrometric and ultraviolet photodiode array detection for analysis of flavonoid glycosides; Rapid Communications in Mass Spectometry 2002; 16: 2341-2348 by Filip Cuyckens and Magda Claeys.
Quantitation of Radiolabeled Compounds Eluting from the HPLC System; Journal of Chromatographic Science, vol. 20, Nov. 1982 by Michael J. Kessler.
Rapid analysis of antibiotic-containing mixtures from fermentation broths by using liquid chromatography-electrospray ionization-mass spectrometry and matrix-assisted laser desorption ionization-time-of-flight-mass spectrometry; American Society for Mass Spectrometry, 1996, 7, 1227-1237 by Bradley L. Ackermann, Brian T. Regg, Luigi Colombo, Sergio Stella, and John E. Coutant.
Application of a xenon arc lamp as a light source for evaporative light scattering detection; Anal Bioanal Chem (2006) 384: 1302-1307 by Karen Guadin etl al.
Enhancement of evaporative light scattering detection in high-performance liquid chromatographic determination of neomycin based on highly volatile mobile phase, high-molecular-mass ion-pairing reagents and controlled peak shape; Journal of Chromatography A 1057 (2004) 125-131 by Nikolaos C. Megoulas et al.
PCT Search Report and Written Opinion for PCT/US2009/006497; Apr. 23, 2010.

* cited by examiner

CHROMATOGRAPHY SYSTEMS AND SYSTEM COMPONENTS

CROSS REFERENCE TO RELATED APPLICATION

This application is a continuation of U.S. patent application Ser. No. 61/201,350.

FIELD OF THE INVENTION

The present invention is directed to chromatography systems and components suitable for use in chromatography systems.

BACKGROUND OF THE INVENTION

There is a need in the art for accurate and efficient reading of machine readable tags (e.g., radio frequency identification (RFID) tags) within a chromatography system. Further, there is a need in the art to efficiently record historical data relating to a given cartridge (e.g., the use history of the cartridge) within a chromatography system.

SUMMARY OF THE INVENTION

The present invention addresses some of the need in the art discussed above by the discovery of new chromatography systems and system components that enable accurate and efficient reading of machine readable tags (e.g., RFID tags) within a chromatography system. In one exemplary embodiment of the present invention, the system component comprises a machine readable tag reader for use in a chromatography system, wherein the machine readable tag reader is operatively adapted to (i) read existing tag data from a machine readable tag; and (ii) write new data onto the machine readable tag. For example, the machine readable tag reader may be used to read existing tag data and write new data on a machine readable tag (e.g., a RFID tag) positioned along a chromatography cartridge. The new data may comprise, for example, historical cartridge use data comprising one or more pieces of data selected from the group consisting of a date of cartridge use, a solvent used in the cartridge on the date, a count of how many times the cartridge has been used, and any combination thereof. The existing tag data may comprise data that sets one or more operational conditions of the chromatography system.

In some embodiments, the system component may comprise a mobile machine readable tag reader suitable for use in a chromatography system, wherein the mobile machine readable tag reader comprises a reader arm having a first end and a second end, the first end being connectable to an object within the chromatography system, and the second end being operatively adapted to move relative to the object when the first end is connected to the object; and a tag reader component attached to the second end, wherein the tag reader component is operatively adapted to (i) move relative to the second end, (ii) read existing tag data from a machine readable tag, and (iii) write new data onto the machine readable tag.

In another exemplary embodiment of the present invention, the system component comprises a fraction collection system of a chromatography system, wherein the fraction collection system comprises a fraction collector tray bay; and one or more sensors positioned along one or more bay wall surfaces of the fraction collector tray bay, the one or more sensors being operatively adapted to detect one or more fraction collector trays positioned within the fraction collector tray bay. For example, one or more (or each) of the one or more sensors may comprise an optical sensor. The exemplary fraction collection system may further comprise one or more stationary machine readable tag readers positioned along the one or more bay wall surfaces of the fraction collector tray bay, wherein each of the one or more stationary machine readable tag readers is operatively adapted to read existing tag data from a machine readable tag on a tray surface of a fraction collector tray.

The system component may comprise a fraction collection system of a chromatography system, wherein the fraction collection system comprises a fraction collector tray bay; one or more stationary machine readable tag readers positioned along one or more bay wall surfaces of the fraction collector tray bay, wherein each of the one or more stationary machine readable tag readers is operatively adapted to read existing tag data from a machine readable tag on a tray surface of a fraction collector tray; and one or more fraction collector trays configured to be positioned within the fraction collector tray bay, wherein each of the one or more fraction collector trays comprises a single machine readable tag positioned along a tray surface of the fraction collector tray.

The present invention is also directed to chromatography systems comprising one or more system components disclosed herein. In one exemplary embodiment of the present invention, the chromatography system comprises a machine readable tag reader, wherein the machine readable tag reader is operatively adapted to (i) read existing tag data from a machine readable tag; and (ii) write new data onto the machine readable tag. In some embodiments, the machine readable tag reader is a mobile machine readable tag reader comprising a tag reader component that is operatively adapted to move so as to position an outer surface of the tag reader component adjacent to and over an outer surface of a given machine readable tag. These exemplary chromatography systems may further comprise one or more machine readable tags alone or in combination with (i) one or more chromatography cartridges, (ii) one or more fraction collector tray bays, or both (i) and (ii). For example, the one or more machine readable tags may be individually positioned along (i) a surface of a given chromatography cartridge, (ii) a surface of a given fraction collector tray bay, or both (i) and (ii). In another exemplary embodiment according to the invention, the chromatography system comprises a machine readable tag reader and a machine readable tag, wherein the machine readable tag reader is operatively adapted to write new data onto the machine readable tag.

In another exemplary embodiment of the present invention, the chromatography system comprises a fraction collection system comprising a fraction collector tray bay; and one or more sensors (e.g., optical sensors) positioned along one or more bay wall surfaces of the fraction collector tray bay, the one or more sensors being operatively adapted to detect one or more fraction collector trays positioned within the fraction collector tray bay.

The chromatography system may comprise a fraction collection system comprising a fraction collector tray bay; one or more stationary machine readable tag readers positioned along one or more bay wall surfaces of the fraction collector tray bay, wherein each of the one or more stationary machine readable tag readers is operatively adapted to read existing tag data from a machine readable tag on a tray surface of a fraction collector tray; and one or more fraction collector trays configured to be positioned within the fraction collector tray bay, wherein each of the one or more fraction collector trays comprises a single machine readable tag positioned along a tray surface of the fraction collector tray.

In some exemplary embodiments of the present invention, the chromatography system comprises at least one mobile machine readable tag reader and in combination with at least one stationary machine readable tag reader, wherein each machine readable tag reader is operatively adapted to read existing tag data from a machine readable tag. In some embodiments, one or more (or each) machine readable tag reader is also operatively adapted to write new tag data onto a given machine readable tag. These exemplary chromatography systems may further comprise one or more machine readable tags alone or in combination with (i) one or more chromatography cartridges, (ii) one or more fraction collector tray bays, or both (i) and (ii). For example, the one or more machine readable tags may be individually positioned along (i) a surface of a given chromatography cartridge, and (ii) a surface of a given fraction collector tray so as to be the only machine readable tag on a given chromatography cartridge or a given fraction collector tray.

In a further exemplary embodiment of the present invention, the chromatography system comprises (1) a fraction collection system comprising (i) a fraction collector tray bay; (ii) one or more stationary machine readable tag readers positioned along one or more bay wall surfaces of the fraction collector tray bay, wherein each of the one or more stationary machine readable tag readers is operatively adapted to read existing tag data from a machine readable tag on a surface of a fraction collector tray; and (iii) one or more fraction collector trays configured to be positioned within the fraction collector tray bay, wherein each of the one or more fraction collector trays comprises a single machine readable tag positioned along a tray surface of the fraction collector tray; and (2) at least one mobile machine readable tag reader, wherein each mobile machine readable tag reader is operatively adapted to read existing tag data from a machine readable tag. In some embodiments, one or more (or each) machine readable tag readers of the chromatography system (i.e., stationary and/or mobile) is operatively adapted to write new tag data onto one or more machine readable tags within the chromatography system.

In yet another exemplary embodiment of the present invention, the chromatography system comprises (1) a fraction collection system comprising a fraction collector tray bay; and one or more stationary machine readable tag readers positioned along one or more bay wall surfaces of the fraction collector tray bay, each of the one or more stationary machine readable tag readers being operatively adapted to read existing tag data from a machine readable tag on a surface of a fraction collector tray; and (2) at least one mobile machine readable tag reader, wherein each mobile machine readable tag reader is operatively adapted to read existing tag data from a machine readable tag on a surface of a chromatography cartridge. In some embodiments, one or more (or each) of the machine readable tag readers of the chromatography system (i.e., stationary and/or mobile) is operatively adapted to write new tag data onto one or more machine readable tags within the chromatography system.

In another exemplary embodiment of the present invention, the chromatography system comprises (1) a fraction collection system comprising (i) a fraction collector tray bay; (ii) one or more sensors (e.g., optical sensors) positioned along one or more bay wall surfaces of the fraction collector tray bay, the one or more sensors being operatively adapted to detect one or more fraction collector trays positioned within the fraction collector tray bay; (iii) one or more stationary machine readable tag readers positioned along the one or more bay wall surfaces of the fraction collector tray bay, each of the one or more stationary machine readable tag readers being operatively adapted to read existing tag data from a machine readable tag on a surface of a fraction collector tray; and (iv) one or more fraction collector trays configured to be positioned within the fraction collector tray bay, wherein each of the one or more fraction collector trays comprises at least one machine readable tag (typically, a single tag) positioned along a tray surface of the fraction collector tray; (2) at least one mobile machine readable tag reader, wherein each mobile machine readable tag reader is operatively adapted to read existing tag data from a machine readable tag on a surface of a chromatography cartridge; and (3) at least one chromatography cartridge, wherein each chromatography cartridge has at least one machine readable tag (typically, a single tag) positioned along a surface of the chromatography cartridge. In some embodiments, one or more (or each) of the machine readable tag readers of the chromatography system (i.e., stationary and/or mobile) is operatively adapted to write new tag data onto one or more machine readable tags within the chromatography system (e.g., a tag on a fraction collector tray and/or a tag on a chromatography cartridge).

The present invention is further directed to methods of making chromatography systems and system components within a chromatography system. In one exemplary method, the method of making a chromatography system comprises incorporating a machine readable tag reader into the chromatography system, wherein the machine readable tag reader is operatively adapted to (i) read existing tag data from a machine readable tag; and (ii) write new data onto the machine readable tag. The method may further comprise incorporating (i) one or more chromatography cartridges, (ii) one or more fraction collector trays, or (iii) both (i) to (ii) into the chromatography system, wherein each chromatography cartridge and/or fraction collector tray comprises at least one machine readable tag (typically one) thereon.

In another exemplary method, the method of making a chromatography system comprises incorporating a mobile machine readable tag reader into the chromatography system, wherein the mobile machine readable tag reader comprises a reader arm having a first end and a second end, the first end being connectable to an object within the chromatography system, and the second end being operatively adapted to move relative to the object when the first end is connected to the object; and a tag reader component attached to the second end, wherein the tag reader component is operatively adapted to (i) move relative to the second end, (ii) read existing tag data from a machine readable tag, and (iii) write new data onto the machine readable tag. The method may further comprise incorporating (i) one or more chromatography cartridges, (ii) one or more fraction collector trays, or (iii) both (i) to (ii) into the chromatography system, wherein each chromatography cartridge and/or fraction collector tray comprises at least one machine readable tag (typically one) thereon.

In yet another exemplary method, the method of making a chromatography system comprises incorporating a fraction collection system into the chromatography system, wherein the fraction collection system comprises a fraction collector tray bay; and one or more sensors (e.g., one or more optical sensors) positioned along one or more bay wall surfaces of the fraction collector tray bay, the one or more sensors being operatively adapted to detect one or more fraction collector trays positioned within the fraction collector tray bay. The exemplary method may further comprise incorporating into the chromatography system one or more stationary machine readable tag readers positioned along the one or more bay wall surfaces of the fraction collector tray bay, wherein each of the one or more stationary machine readable tag readers is operatively adapted to read existing tag data from a machine readable tag on a tray surface of a fraction collector tray. The exemplary method may even further comprise incorporating into the chromatography system one or more fraction collector trays configured to be positioned within the fraction collector tray bay, wherein each of the one or more fraction collector trays comprises at least one machine readable tag (typically, a single tag) positioned along a tray surface of the fraction collector tray.

In another exemplary method, the method of making a chromatography system comprises incorporating a fraction collection system into the chromatography system, wherein the fraction collection system comprises a fraction collector tray bay; one or more stationary machine readable tag readers positioned along one or more bay wall surfaces of the fraction collector tray bay, wherein each of the one or more stationary machine readable tag readers is operatively adapted to read existing tag data from a machine readable tag on a tray surface of a fraction collector tray; and one or more fraction collector trays configured to be positioned within the fraction collector tray bay, wherein each of the one or more fraction collector trays comprises a single machine readable tag positioned along a tray surface of the fraction collector tray.

In another exemplary method, the method of making a chromatography system comprises incorporating a fraction collection system into the chromatography system, wherein the fraction collection system comprises (i) a fraction collector tray bay; (ii) one or more stationary machine readable tag readers positioned along one or more bay wall surfaces of the fraction collector tray bay, wherein each of the one or more stationary machine readable tag readers is operatively adapted to read existing tag data from a machine readable tag on a surface of a fraction collector tray; and (iii) one or more fraction collector trays configured to be positioned within the fraction collector tray bay, wherein each of the one or more fraction collector trays comprises a single machine readable tag positioned along a tray surface of the fraction collector tray; and incorporating at least one mobile machine readable tag reader into the chromatography system, wherein each mobile machine readable tag reader is operatively adapted to read existing tag data from a machine readable tag. In some embodiments, one or more (or each) machine readable tag readers of the resulting chromatography system (i.e., stationary and/or mobile) is operatively adapted to write new tag data onto one or more machine readable tags within the chromatography system.

In yet another exemplary method, the method of making a chromatography system comprises incorporating a fraction collection system into the chromatography system, wherein the fraction collection system comprises a fraction collector tray bay; and one or more stationary machine readable tag readers positioned along one or more bay wall surfaces of the fraction collector tray bay, each of the one or more stationary machine readable tag readers being operatively adapted to read existing tag data from a machine readable tag on a surface of a fraction collector tray; incorporating one or more chromatography cartridges into the chromatography system; and incorporating at least one mobile machine readable tag reader into the chromatography system, wherein each mobile machine readable tag reader is operatively adapted to read existing tag data from a machine readable tag on a surface of the one or more chromatography cartridges.

In yet another exemplary method, the method of making a chromatography system comprises (1) incorporating a fraction collection system into the chromatography system, wherein the fraction collection system comprises (i) a fraction collector tray bay; (ii) one or more sensors (e.g., optical sensors) positioned along one or more bay wall surfaces of the fraction collector tray bay, the one or more sensors being operatively adapted to detect one or more fraction collector trays positioned within the fraction collector tray bay; (iii) one or more stationary machine readable tag readers positioned along the one or more bay wall surfaces of the fraction collector tray bay, each of the one or more stationary machine readable tag readers being operatively adapted to read existing tag data from a machine readable tag on a surface of a fraction collector tray; and (iv) one or more fraction collector trays configured to be positioned within the fraction collector tray bay, wherein each of the one or more fraction collector trays comprises at least one machine readable tag (typically, a single tag) positioned along a tray surface of the fraction collector tray; (2) incorporating at least one mobile machine readable tag reader into the chromatography system, wherein each mobile machine readable tag reader is operatively adapted to read existing tag data from a machine readable tag on a surface of a chromatography cartridge; and (3) incorporating at least one chromatography cartridge into the chromatography system, wherein each chromatography cartridge has at least one machine readable tag (typically, a single tag) positioned along a surface of the chromatography cartridge. In some embodiments, one or more (or each) of the machine readable tag readers of the resulting chromatography system (i.e., stationary and/or mobile) is operatively adapted to write new tag data onto one or more machine readable tags within the chromatography system (e.g., a tag on a fraction collector tray and/or a tag on a chromatography cartridge).

The present invention is further directed to methods of making system components within a chromatography system. In one exemplary embodiment, the method of making a system component comprises incorporating one or more sensors (e.g., one or more optical sensors) into a fraction collection system. The method may comprise positioning one or more sensors (e.g., one or more optical sensors) along one or more bay wall surfaces of a fraction collector tray bay, the one or more sensors being operatively adapted to detect one or more fraction collector trays positioned within the fraction collector tray bay. The method may further comprise positioning one or more stationary machine readable tag readers along the one or more bay wall surfaces of the fraction collector tray bay, wherein each of the one or more stationary machine readable tag readers is operatively adapted to read existing tag data from a machine readable tag on a tray surface of a fraction collector tray. The method may even further comprise forming one or more fraction collector trays configured to be positioned within the fraction collector tray bay, wherein each of the one or more fraction collector trays comprises at least one machine readable tag (typically, a single tag) positioned along a tray surface of the fraction collector tray.

In another exemplary embodiment, the method of making a system component comprises positioning one or more stationary machine readable tag readers along one or more bay wall surfaces of a fraction collector tray bay, wherein each of the one or more stationary machine readable tag readers is operatively adapted to read existing tag data from a machine readable tag on a tray surface of a fraction collector tray; and forming one or more fraction collector trays configured to be positioned within the fraction collector tray bay, wherein each of the one or more fraction collector trays comprises a single machine readable tag positioned along a tray surface of the fraction collector tray. In some embodiments, the step of forming one or more fraction collector trays comprises forming fraction collector trays configured to be positioned in a side-by-side arrangement within the fraction collector tray bay so that an outer perimeter of at least two side-by-side fraction collector trays each independently abut two adjacent bay side wall surfaces when positioned within the fraction collector tray bay.

The present invention is even further directed to methods of using chromatography systems and system components within a chromatography system. In one exemplary method, the method of using a system component comprises reading existing tag data from a machine readable tag within a chromatography system via a machine readable tag reader; and writing new data onto the machine readable tag within the chromatography system via the machine readable tag reader. The steps of reading existing tag data and writing new data may comprise reading existing tag data and writing new data on a machine readable tag (e.g., a RFID tag) positioned along a chromatography cartridge. For example, the step of writing new data may comprise writing new data onto the chromatography cartridge tag such as historical cartridge use data comprising one or more pieces of data selected from the group consisting of a date of cartridge use, a solvent used in the cartridge on the date, a count of how many times the cartridge has been used, and any combination thereof. The step of reading existing tag data from the chromatography cartridge tag may comprise reading data that sets one or more operational conditions of the chromatography system.

In another exemplary method, the method of using a system component comprises reading existing tag data from a machine readable tag within a chromatography system via a mobile machine readable tag reader; and writing new data onto the machine readable tag within the chromatography system via the mobile machine readable tag reader. The mobile machine readable tag reader may comprise a reader arm having a first end and a second end, the first end being connectable to an object within the chromatography system, and the second end being operatively adapted to move relative to the object when the first end is connected to the object; and a tag reader component attached to the second end, wherein the tag reader component is operatively adapted to (i) move relative to the second end, (ii) read existing tag data from a machine readable tag, and (iii) write new data onto the machine readable tag.

In yet another exemplary method, the method of using a system component comprises utilizing one or more sensors (e.g., one or more optical sensors) to detect one or more fraction collector trays positioned within a fraction collector tray bay of a fraction collection system within a chromatography system. The one or more sensors may be positioned along one or more bay wall surfaces of the fraction collector tray bay so as to detect the presence or absence of one or more fraction collector trays positioned within the fraction collector tray bay. The exemplary method of using a system component may further comprise utilizing one or more stationary machine readable tag readers positioned along the one or more bay wall surfaces of the fraction collector tray bay to read existing tag data from a machine readable tag on a tray surface of a fraction collector tray.

In a further exemplary method, the method of using a system component comprises utilizing one or more stationary machine readable tag readers positioned along one or more bay wall surfaces of a fraction collector tray bay to read existing tag data from a machine readable tag on a tray surface of a fraction collector tray; and collecting one or more sample fractions within one or more collection vessels positioned at one or more specific locations along the fraction collector tray based on the existing tag data. Typically, each fraction collector tray within the chromatography system comprises a single machine readable tag positioned along an abutting tray surface (i.e., a tray surface that abuts a bay wall surface of the fraction collector tray bay) of a given fraction collector tray.

In some embodiments, the method of using a system component may comprise utilizing one or more system components in a chromatography system, wherein the method comprises utilizing at least one mobile machine readable tag reader and in combination with at least one stationary machine readable tag reader within the chromatography system, wherein each machine readable tag reader is operatively adapted to read existing tag data from a machine readable tag, and at least one (or each) of the machine readable tag readers is also operatively adapted to write new tag data onto a given machine readable tag within the chromatography system. The exemplary methods may further comprise utilizing one or more machine readable tags within the chromatography system either alone or in combination with (i) one or more chromatography cartridges, (ii) one or more fraction collector tray bays, or both (i) and (ii).

In yet a further exemplary method, the method of using a system component comprises utilizing one or more system components in a chromatography system, wherein the method comprises (1) utilizing one or more sensors (e.g., one or more optical sensors) to detect one or more fraction collector trays positioned within a fraction collector tray bay of a fraction collection system within a chromatography system; (2) utilizing one or more stationary machine readable tag readers positioned along one or more bay wall surfaces of the fraction collector tray bay to read existing tag data from a machine readable tag on a tray surface of a fraction collector tray; (3) collecting one or more sample fractions within one or more collection vessels positioned at one or more specific locations along the fraction collector tray based on the existing tag data; (4) utilizing at least one mobile machine readable tag reader within the chromatography system, wherein each mobile machine readable tag reader is operatively adapted to read existing tag data from a machine readable tag on a surface of a chromatography cartridge; and (5) utilizing at least one chromatography cartridge within the chromatography system, wherein each chromatography cartridge has at least one machine readable tag (typically, a single tag) positioned along a surface of the chromatography cartridge. In some embodiments, one or more (or each) of the machine readable tag readers of the chromatography system (i.e., stationary and/or mobile) is operatively adapted to also write new tag data onto one or more machine readable tags within the chromatography system (e.g., a tag on a fraction collector tray and/or a tag on a chromatography cartridge).

These and other features and advantages of the present invention will become apparent after a review of the following detailed description of the disclosed embodiments and the appended claims.

DETAILED DESCRIPTION OF THE INVENTION

Figure 1:
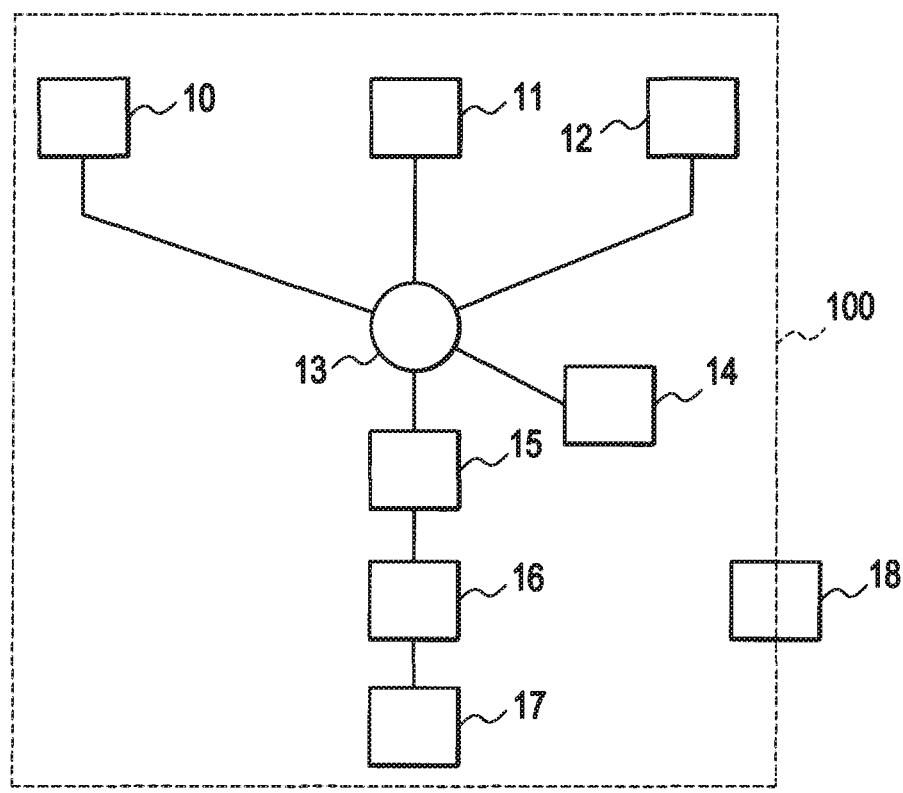
FIG. 1 depicts a schematic diagram of an exemplary chromatography system of the present invention and individual system components within the exemplary chromatography system.

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

It must be noted that as used herein and in the appended claims, the singular forms "a", "and", and "the" include plural referents unless the context clearly dictates otherwise. Thus, for example, reference to "a solvent" includes a plurality of such solvents and reference to "solvent" includes reference to one or more solvents and equivalents thereof known to those skilled in the art, and so forth.

"About" modifying, for example, the quantity of an ingredient in a composition, concentrations, volumes, process temperatures, process times, recoveries or yields, flow rates, and like values, and ranges thereof, employed in describing the embodiments of the disclosure, refers to variation in the numerical quantity that may occur, for example, through typical measuring and handling procedures; through inadvertent error in these procedures; through differences in the ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

As used herein, the term "chromatography" means a physical method of separation in which the components to be separated are distributed between two phases, one of which is stationary (stationary phase) while the other (the mobile phase) moves in a definite direction.

As used herein, the term "liquid chromatography" means the separation of mixtures by passing a fluid mixture dissolved in a "mobile phase" through a column comprising a stationary phase, which separates the analyte (i.e., the target substance) from other molecules in the mixture and allows it to be isolated.

As used herein, the term "mobile phase" means a fluid liquid, a gas, or a supercritical fluid that comprises the sample being separated and/or analyzed and the solvent that moves the sample comprising the analyte through the column. The mobile phase moves through the chromatography column or cartridge (i.e., the container housing the stationary phase) where the analyte in the sample interacts with the stationary phase and is separated from the sample.

As used herein, the term "stationary phase" or "media" means material fixed in the column or cartridge that selectively adsorbs the analyte from the sample in the mobile phase separation of mixtures by passing a fluid mixture dissolved in a "mobile phase" through a column comprising a stationary phase, which separates the analyte to be measured from other molecules in the mixture and allows it to be isolated.

As used herein, the term "flash chromatography" means the separation of mixtures by passing a fluid mixture dissolved in a "mobile phase" under pressure through a column comprising a stationary phase, which separates the analyte (i.e., the target substance) from other molecules in the mixture and allows it to be isolated.

As used herein, the term "fluid" means a gas, liquid, and supercritical fluid.

As used herein, the term "substantially" means within a reasonable amount, but includes amounts which vary from about 0% to about 50% of the absolute value, from about 0% to about 40%, from about 0% to about 30%, from about 0% to about 20% or from about 0% to about 10%.

The present invention is directed to chromatography systems and individual system components that may be used in chromatography systems either alone or in combination with one another. The present invention is further directed to methods of making chromatography systems and individual system components that may be used in chromatography systems. The present invention is even further directed to methods of using chromatography systems, as well as methods of using individual system components within a variety of chromatography systems. One exemplary chromatography system containing individual system components of the present invention is shown in FIG. 1.

As shown in FIG. 1, exemplary chromatography system 100 comprises a sample injection apparatus 10, a mobile phase source 11, an air source 12, a valve 13, a waste collector 14, a column station 15, a detector 16 (e.g., a UV detector), a fraction collection system 17, and a microprocessor 18. The present invention provides individual system components that are particularly suitable for use within column station 15, fraction collection system 17, or both column station 15 and fraction collection system 17 of exemplary chromatography system 100, as well as chromatography systems containing a column station and/or a fraction collection system. A description of the individual system components of the present invention, as well as chromatography systems containing the individual system components is provided below.

It should be noted that other chromatography system components disclosed in exemplary chromatography system 100 (e.g., sample injection apparatus 10, mobile phase source 11, air source 12, valve 13, waste collector 14, detector 16, and microprocessor 18) may comprise known components. For example, sample injection apparatus 10 and valve 13 may respectively comprise any known sample injection apparatus and valve used in chromatography systems. In some embodiments, sample injection apparatus 10 may comprise an automated sample injection apparatus and valve 13 may comprise a six port rotary valve as disclosed in U.S. Provisional Patent Application Ser. No. 61/201,351, entitled "AUTOMATED SAMPLE INJECTION APPARATUS, MULTIPORT VALVE, AND METHODS OF MAKING AND USING THE SAME" and filed on Dec. 10, 2008, the subject matter of which is incorporated herein in its entirety.

Further, it should be noted that although not shown in FIG. 1, exemplary chromatography system 100 comprises one or more additional components typically present in a given chromatography system so as to provide for fluid flow throughout the chromatography system between the various components of a given chromatography system. For example, exemplary chromatography system 100 may comprise one or more additional components including, but not limited to, one or more pumps, one or more additional valves, tubing between components, electronics and electronic circuitry to power and control the various components, etc.

I. Chromatography System Components and Configurations

The chromatography systems of the present invention may comprise one or more of the following individual system components in a variety of chromatography system configurations.

A. Chromatography System Components

The chromatography systems of the present invention may comprise one or more of the following individual system components.

1. Machine Readable Tag Readers/Writers

The chromatography systems of the present invention may comprise one or more machine readable tag readers. In some embodiments, at least one machine readable tag reader is operatively adapted to (i) read existing tag data from a machine readable tag (e.g., a RFID tag); and (ii) write new data onto the same machine readable tag. For example, when the machine readable tag is present on a cartridge (also referred to herein as a column) used in the chromatography system, the new data written to the machine readable tag may comprise historical cartridge use data. The historical cartridge use data may comprise one or more pieces of data including, but not limited to, data including the date of cartridge use, a solvent used in the cartridge on the date, a count of how many times the cartridge has been used, sample type, user name, and any combination thereof.

The existing tag data on a given machine readable tag (e.g., the above-described cartridge machine readable tag) may comprise data that sets one or more operational conditions of the chromatography system. For example, when the machine readable tag is present on a cartridge used in the chromatography system, the new data written to the machine readable tag may comprise data including, but not limited to, the cartridge size, the solid phase material (e.g., silica) within the cartridge, the mobile phase (i.e., solvent) to be used with the cartridge in an upcoming run, operating temperatures, flow rates, other operational conditions to run the cartridge in the system, and any combination thereof.

The machine readable tag readers used in the present invention may be mobile machine readable tag readers or stationary machine readable tag readers. As used herein, the term "mobile" is used to describe a machine readable tag reader that comprises a tag reader component that is operatively adapted to move from an initial location to a reading location during the step of reading a given machine readable tag. The mobile machine readable tag reader of the present invention comprises a tag reader component that is operatively adapted to move so as to position an outer surface of the tag reader component adjacent to and over an outer surface of the machine readable tag. In contrast, stationary machine readable tag readers used in the present invention do not move. In order to read a given machine readable tag using a stationary machine readable tag reader, the machine readable tag has to be moved so that the machine readable tag is positioned in front of a tag reader component of the stationary machine readable tag reader. The tag read, writer and tag may be composed of any suitable media including magnetic media, bar code, solid state memory, polycarbonate, etc.

Figure 2:
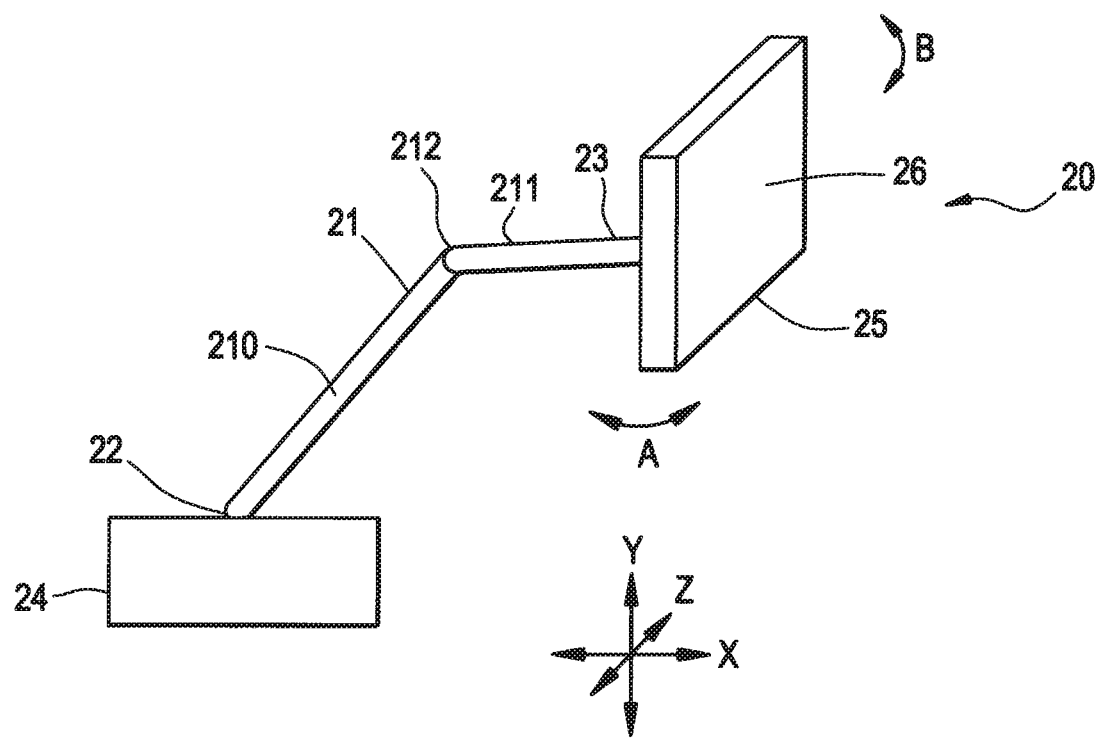
FIG. 2 depicts an exemplary mobile machine readable tag reader of the present invention suitable for use in the exemplary chromatography system shown in FIG. 1.

FIG. 2 depicts an exemplary mobile machine readable tag reader of the present invention. As shown in FIG. 2, exemplary mobile machine readable tag reader 20 comprises (i) a reader arm 21 having a first end 22 and a second end 23 with first end 22 being connectable to an object 24 within the chromatography system (e.g., an object within column station 15 of exemplary chromatography system 100), and second end 23 being operatively adapted to move relative to object 24 when first end 22 is connected to object 24; and (ii) a tag reader component 25 attached to second end 23, wherein tag reader component 25 is operatively adapted to (i) move relative to second end 23, (ii) read existing tag data from a machine readable tag (not shown), and (iii) write new data onto the machine readable tag. Exemplary tag reader component 25 is operatively adapted to move so as to position an outer surface 26 of tag reader component 25 adjacent to and over an outer surface of a machine readable tag (not shown).

As shown in FIG. 2, exemplary mobile machine readable tag reader 20 comprises two reader arm sections, namely, first reader arm section 210 and second reader arm section 211 joined to one another via arm section connector 212. Typically, arm section connector 212 may move to any three-dimensional coordinate relative to first end 22, second end 23 may move to any three-dimensional coordinate relative to arm section connector 212, and tag reader component 25 may move relative to second end 23 as shown by arrows A and B with arrow A representing movement of an outer surface 26 of tag reader component 25 relative to an axis extending in the y direction (i.e., side-to-side movement), and arrow B representing movement of an outer surface 26 of tag reader component 25 relative to an axis extending in the x direction (i.e., up and down movement).

It should be noted that other exemplary mobile machine readable tag readers suitable for use in the chromatography systems of the present invention may comprise a single reader arm section (i.e., no arm section connector 212) having a first end connected to an object (e.g., object 24) and a second end connected to a tag reader component (e.g., tag reader component 25). In other embodiments, the mobile machine readable tag reader may comprise three or more reader arm sections and two or more arm section connectors.

At least one mobile machine readable tag reader, such as exemplary mobile machine readable tag reader 20, is particularly useful within column station 15 of exemplary chromatography system 100. The at least one mobile machine readable tag reader may be used in combination with one or more machine readable tags. In some desired embodiment, the at least one mobile machine readable tag reader is used in combination with one or more machine readable tags, wherein each machine readable tag is positioned on a separate chromatography cartridge. As noted above, the at least one mobile machine readable tag reader may be operatively adapted to (i) read existing tag data from a machine readable tag (e.g., a RFID tag) on a chromatography cartridge; as well as (ii) write new data onto the same machine readable tag on the chromatography cartridge.

Figure 3:
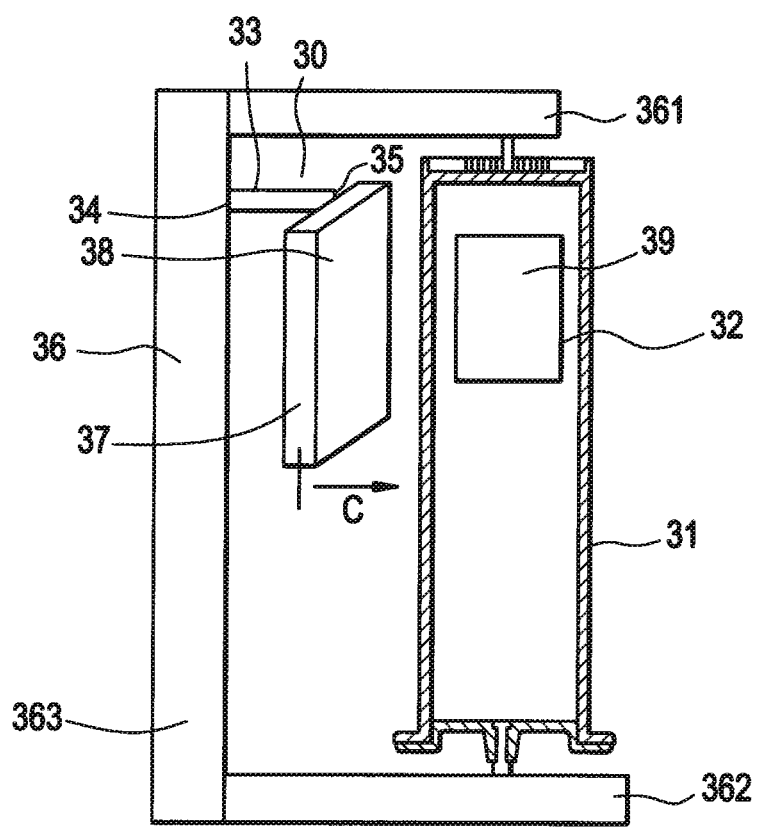
FIG. 3 depicts another exemplary mobile machine readable tag reader in combination with an exemplary chromatography cartridge having thereon an exemplary machine readable tag.

FIG. 3 depicts another exemplary mobile machine readable tag reader 30 in combination with an exemplary chromatography cartridge 31 having thereon an exemplary machine readable tag 32. As shown in FIG. 3, exemplary mobile machine readable tag reader 30 comprises a reader arm 33 having a first end 34 and a second end 35 with first end 34 being connectable to an object 36 within the chromatography system. In this exemplary embodiment, object 36 comprises a cartridge support member comprising a vertically extending member 363 and two horizontally extending members: upper member 361 (also referred to herein as column arm 361) and lower member 362. Object 36 is within a column station such as column station 15 of exemplary chromatography system 100. Second end 35 is operatively adapted to move relative to object 36 when first end 34 is connected to object 36. Exemplary mobile machine readable tag reader 30 further comprises tag reader component 37 attached to second end 35, wherein tag reader component 37 is operatively adapted to (i) move relative to second end 35, (ii) read existing tag data from machine readable tag 32, and (iii) write new data onto machine readable tag 32.

As shown in FIG. 3, tag reader component 37 of exemplary mobile machine readable tag reader 30 is operatively adapted to move in a direction as shown by arrow C so as to position an outer surface 38 of tag reader component 37 adjacent to column or cartridge 31 and near or over an outer surface 39 of machine readable tag 32. Desirably, tag reader component 37 of exemplary mobile machine readable tag reader 30 is operatively adapted to identify a location of machine readable tag 32, and move as needed to position an outer surface 38 of tag reader component 37 adjacent to and over an outer surface 39 of machine readable tag 32.

Chromatography systems of the present invention may also comprise one or more stationary machine readable tag readers alone or in combination with one or more mobile machine readable tag readers. As discussed further below, in some embodiments of the present invention, a given chromatography system may comprise at least one mobile machine readable tag reader and/or at least one stationary machine readable tag reader in combination with (1) one or more machine readable tags, and (2) (i) a chromatography cartridge, (ii) a fraction collector tray bay, or both (i) the chromatography cartridge and (ii) the fraction collector tray bay, wherein the one or more machine readable tags are positioned along a surface of the chromatography cartridge, a surface of the fraction collector tray bay, or both. One or more stationary machine readable tag readers are particularly useful within a fraction collection system such as exemplary fraction collection system 17 of exemplary chromatography system 100.

2. Fraction Collection Tray Sensors

The chromatography systems of the present invention may comprise one or more fraction collection tray sensors alone or in combination with the herein described machine readable tag readers (e.g., one or more mobile machine readable tag readers, and/or one or more stationary machine readable tag readers, at least one of which may also write new data onto one or more machine readable tags).

In one exemplary embodiment, a chromatography system of the present invention comprises a fraction collection system, wherein the fraction collection system comprises (i) a fraction collector tray bay; and (ii) one or more sensors positioned along one or more bay wall surfaces of the fraction collector tray bay, wherein the one or more sensors are operatively adapted to detect one or more fraction collector trays positioned within the fraction collector tray bay. In some embodiments, at least one of the one or more sensors comprises an optical sensor. For example, during operation, a user may decide to remove a tray from the fraction collector tray bay. By positioning one or more sensors in the fraction collector tray bay, the fraction collection system automatically shuts down (or pauses) a given operation when the sensor detects that the tray has been removed, and remains shut down or paused until the tray is returned to the fraction collector tray bay.

In some embodiments, the fraction collection system further comprises one or more stationary machine readable tag readers positioned along the one or more bay wall surfaces of the fraction collector tray bay, wherein each of the one or more stationary machine readable tag readers is operatively adapted to read existing tag data from a machine readable tag on a surface of a fraction collector tray. At least one of the one or more stationary machine readable tag readers may be operatively adapted to also write new data onto a given machine readable tag on a surface of a fraction collector tray.

Figure 4:
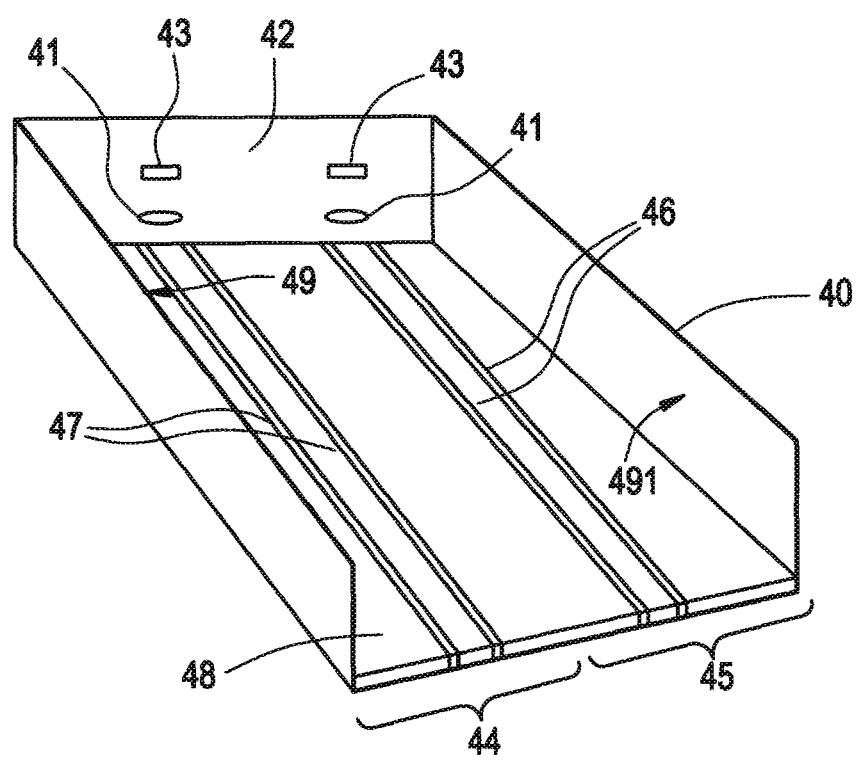
FIG. 4 depicts an exemplary fraction collector tray bay suitable for use in a fraction collection system within the exemplary chromatography system shown in FIG. 1.

FIG. 4 depicts an exemplary fraction collector tray bay suitable for use in fraction collection system 17 within exemplary chromatography system 100 shown in FIG. 1. As shown in FIG. 4, exemplary fraction collector tray bay 40 comprises one or more sensors 41 positioned along bay wall surface 42 of fraction collector tray bay 40. Each sensor 41 is operatively adapted to detect a fraction collector tray (e.g., exemplary fraction collector tray 50 shown in FIG. 5) positioned within fraction collector tray bay 40. Exemplary fraction collector tray bay 40 also comprises stationary machine readable tag readers 43 positioned along bay wall surface 42 of fraction collector tray bay 40. Each of stationary machine readable tag readers 43 is operatively adapted to read existing tag data from a machine readable tag on a surface of a fraction collector tray (e.g., machine readable tag 51 on surface 52 of fraction collector tray 50 shown in FIG. 5). Each of stationary machine readable tag readers 43 may also be operatively adapted to write new data onto a given machine readable tag on a surface of a fraction collector tray (e.g., machine readable tag 51 on surface 52 of fraction collector tray 50 shown in FIG. 5).

One or more fraction collector trays are configured to be positioned within fraction collector tray bay 40, along track 44 and/or track 45 shown in FIG. 4. Each of tracks 44 and 45 comprise one or more grooves 47 within lower bay surface 48 so that corresponding tray extension on a given fraction collector tray can extend into grooves 47 as to guide the given fraction collector tray into fraction collector tray bay 40.

Figure 5:
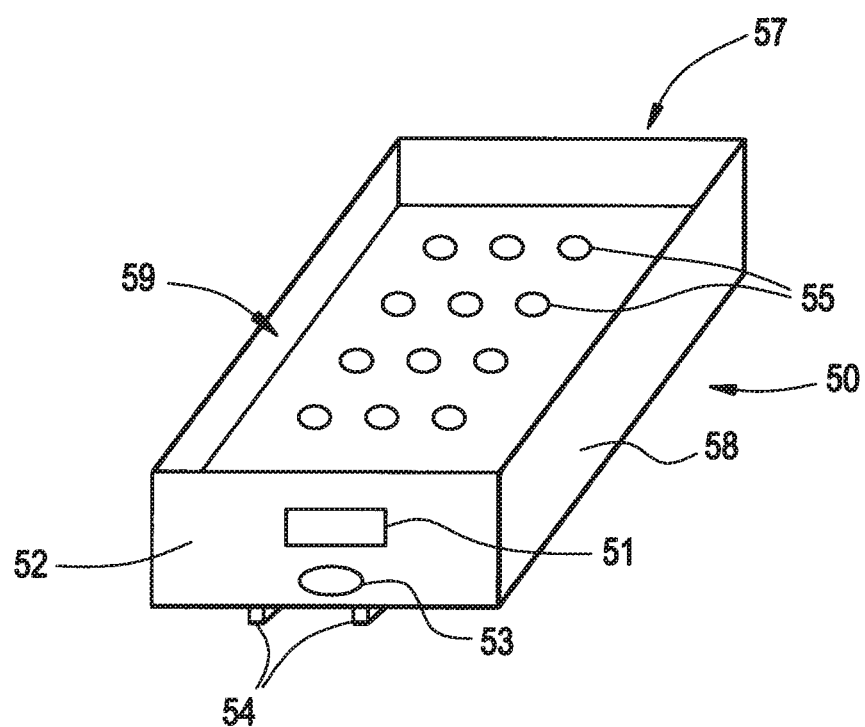
FIG. 5 depicts an exemplary fraction collector tray used in the exemplary fraction collector tray bay shown in FIG. 4.

FIG. 5 depicts an exemplary fraction collector tray configured for use in exemplary fraction collector tray bay 40 shown in FIG. 4. As shown in FIG. 5, exemplary fraction collector tray 50 comprises machine readable tag 51 positioned along tray surface 52. When positioned within fraction collector tray bay 40, tray surface 52 of exemplary fraction collector tray 50 faces and is positioned directly in front of one of stationary machine readable tag readers 43 positioned along bay wall surface 42 of fraction collector tray bay 40. As noted above, tray extensions 54 on exemplary fraction collector tray 50 can extend into grooves 47 as to guide exemplary fraction collector tray 50 into fraction collector tray bay 40.

Exemplary fraction collector tray 50 also comprises sensor tab 53 positioned along tray surface 52. When positioned within fraction collector tray bay 40, sensor tab 53 of exemplary fraction collector tray 50 faces and is positioned directly in front of one of sensors 41 positioned along bay wall surface 42 of fraction collector tray bay 40. Sensor tab 53 provides a signal to microprocessor 18 that exemplary fraction collector tray 50 is present within fraction collector tray bay 40, and the fraction collection system is equipped to receive more fractions.

Exemplary fraction collector tray 50 further comprises fraction vessel positions 55 along an outer tray surface 56 of exemplary fraction collector tray 50. Each fraction vessel position 55 is sized so as to position a fraction vessel (e.g., test tube) (not shown) along an upper surface 56 of exemplary fraction collector tray 50. Exemplary fraction collector tray 50 may further comprise one or more additional features including, but not limited to, a tray handle (not shown) along tray surface 57.

Exemplary fraction collector tray 50 may comprise one or more machine readable tags (e.g., machine readable tag 51). In some embodiments, each fraction collector tray 50 comprises a single machine readable tag 51 positioned along tray surface 52 of fraction collector tray 50. The single machine readable tag 51 may comprise fraction/tray data, wherein the fraction/tray data comprising (i) fraction vessel positions/locations 55 along an outer tray surface 56 of exemplary fraction collector tray 50, (ii) empty fraction vessel positions 55 along an outer tray surface 56 of exemplary fraction collector tray 50, (iii) occupied fraction vessel positions 55 along an outer tray surface 56 of exemplary fraction collector tray 50, (iv) fraction vessel information for each fraction vessel positioned within one or more of the occupied fraction vessel positions 55, (v) fraction information for each fraction positioned within one or more of the occupied fraction vessel positions 55, (vi) a unique identification of a given tray, (vii) a fraction vessel (i.e., vial) size, (viii) a collectable volume for each fraction vessel (i.e., vial), (ix) the last time the tray was used, and (x) any combination of (i) to (ix).

Each exemplary fraction collector tray 50 and exemplary fraction collector tray bay 40 may be sized and configured so that a desired number of exemplary fraction collector trays 50 are positionable within exemplary fraction collector tray bay 40. As shown in FIG. 4, in some desired embodiments, at least two fraction collector trays (e.g., two exemplary fraction collector trays 50) are positionable in a side-by-side arrangement relative to one another, and an outer perimeter of at least two side-by-side fraction collection trays (e.g., two exemplary fraction collector trays 50) faces at least two adjacent bay wall surfaces of exemplary fraction collector tray bay 40. For example, when two exemplary fraction collector trays 50 are positioned in a side-by-side manner within fraction collector tray bay 40, exemplary fraction collector tray 50 positioned along track 44 has an outer perimeter, namely, tray surfaces 52 and 58, facing adjacent bay wall surfaces 42 and 49 respectively of exemplary fraction collector tray bay 40, while an adjacent exemplary fraction collector tray 50 positioned along track 45 has an outer perimeter, namely, tray surfaces 52 and 59, facing adjacent bay wall surfaces 42 and 491 respectively of exemplary fraction collector tray bay 40.

Although exemplary fraction collector tray bay 40 is shown in FIG. 4 as having only two stationary machine readable tag readers 43, it should be understood that exemplary fraction collector tray bay 40 may comprise any number of stationary machine readable tag readers 43. For example, exemplary fraction collector tray bay 40 may comprise one or more stationary machine readable tag readers 43 along bay wall surfaces 49 and 491, for example, when four or more fraction collector trays 50 are positioned within exemplary fraction collector tray bay 40. Typically, the one or more bay wall surfaces (i.e., bay wall surfaces 49, 42 and 491) comprise a single stationary machine readable tag reader 43 for each fraction collector tray 50 positioned within fraction collector tray bay 40. In one embodiment, a single bay wall surface (e.g., bay wall surface 42) comprises at least two stationary machine readable tag readers 43 for at least two side-by-side fraction collector trays 43. In one desired embodiment, a single bay wall surface (e.g., bay wall surface 42) comprises two stationary machine readable tag readers 43 for two side-by-side fraction collector trays 43.

3. Cartridge Height Sensors

The chromatography columns of the present invention may comprise one or more cartridge height sensors alone or in combination with (1) the herein described machine readable tag readers (e.g., one or more mobile machine readable tag readers, and/or one or more stationary machine readable tag readers, at least one of which may also write new data onto one or more machine readable tags), (2) the herein described fraction collection tray sensors, or (3) both (1) and (2).

Figure 6A:
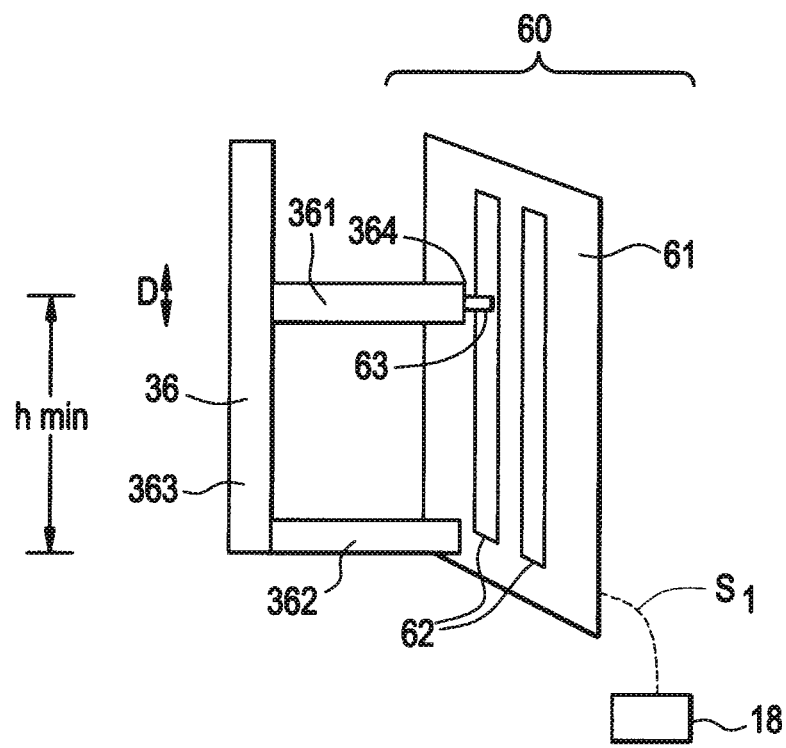
FIG. 6A depicts an exemplary cartridge height sensing device of the present invention suitable for use in the exemplary chromatography system shown in FIG. 1.
Figure 6B:
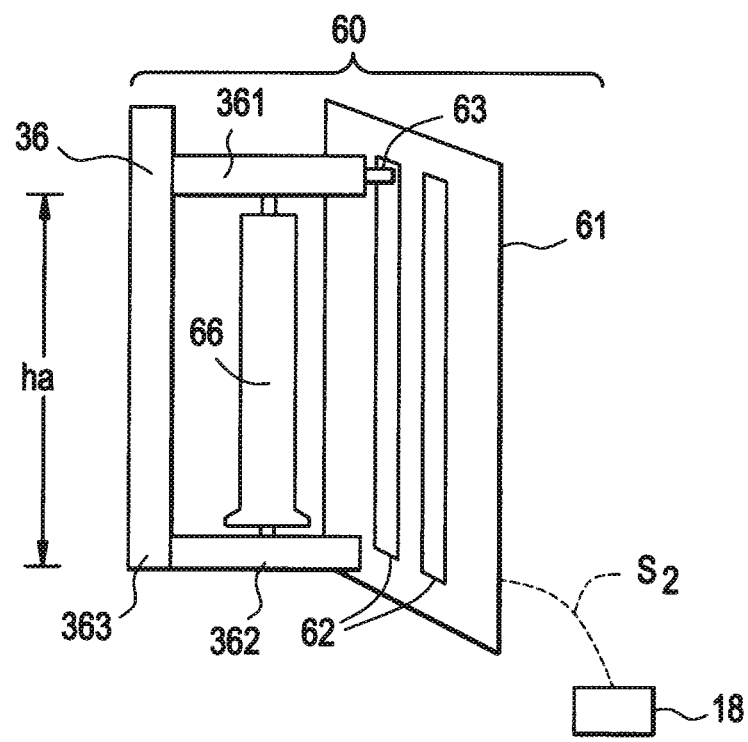
FIG. 6B depicts the exemplary cartridge height sensing device of FIG. 6A while measuring the height of a cartridge.

FIG. 6A depicts an exemplary cartridge height sensing device of the present invention suitable for use, for example, within column station 15 of exemplary chromatography system 100 shown in FIG. 1. As shown in FIG. 6, exemplary cartridge height sensing device 60 comprises a printed circuit board 61, one or more pad sensors 62 extending vertically along printed circuit board 61, and one or more contact sensors 63 positioned along upper member 361 (also referred to herein as column arm 361) of cartridge support member 36. Column arm 361 moves up or down as shown by arrow D to accommodate a cartridge (see FIG. 6B) positioned between column arm 361 and lower member 362. When a cartridge is not present as shown in FIG. 6A, column arm 361 rests in a home position, which corresponds to a minimum height, $h_{min}$.

Contact sensor 63 slides along printed circuit board 61 and contacts one or more of pad sensors 62. The position of contact sensor 63 along one or more of pad sensors 62 causes printed circuit board 61 to send a specific analog signal, shown as dash lines $S_1$, corresponding to the position of contact, to a microprocessor (e.g., microprocessor 18), which converts the specific analog signal $S_1$ into a specific cartridge height.

FIG. 6B depicts exemplary cartridge height sensing device 60 while measuring the height, $h_c$, of exemplary cartridge 66. As shown in FIG. 6B, column arm 361 is moved upward to accommodate cartridge 66 positioned between column arm 361 and lower member 362. In this position, contact sensor 63 in contact with one or more of pad sensors 62 causes printed circuit board 61 to send a specific analog signal, shown as dash lines $S_2$, corresponding to the position of contact, to a microprocessor (e.g., microprocessor 18), which converts the specific analog signal $S_2$ into a specific cartridge height, $h_c$.

Once exemplary cartridge 66 is removed from cartridge support member 36, column arm 361 will automatically slide back down to the home position (i.e., minimum height reading $h_{min}$). The home position is a unique setting that does not match the height value associated with any cartridge (e.g., exemplary cartridge 66) or bypass cartridge. In some embodiments, in order to start a run, column arm 361 and cartridge height sensing device 60 will need to recognize the presence of a cartridge (e.g., exemplary cartridge 66) or bypass cartridge. If column arm 361 and contact sensor 63 has not been moved away from the home position, the system will (i) error and (ii) stop the unit from starting or completing a run.

Cartridge height sensing device 60 is designed to work with a variety of flash cartridges with and without machine readable tags (e.g., RFID inlays). If a non-RFID cartridge (e.g., exemplary cartridge 66) is installed, cartridge height sensing device 60 can use the determined height measurement of the non-RFID cartridge to automatically configure the system to work with the cartridge. For example, a particular height measurement determined by microprocessor 18 may result in microprocessor 18 making one or more process changes to the system configuration. In some embodiments, if an RFID cartridge (e.g., exemplary cartridge 31 shown in FIG. 3) is installed, the read data from the RFID tag is compared with the data collected from cartridge height sensing device 60 and compared. If the collected information does not match, the system will error and the user will have to correct the error before continuing the run. If the information matches, the system will proceed as normal.

Cartridges with RFID inlays (e.g., exemplary cartridge 31 shown in FIG. 3) are specially designed to work at high pressures. If the system does not recognize the RFID inlay, the system will default to the lower column pressures. If the system is setup to work with an RFID (high pressure) cartridge and the cartridge is replaced prior to the run, cartridge height sensing device 60 within the system will recognize the change, check for the absence of an RFID inlay (e.g., machine readable tag, such as machine readable tag 32 shown in FIG. 3), and default to the lower pressure setting. Cartridge height sensing device 60 can be used to prevent a user from using higher-pressure settings on lower pressure rated cartridges.

Although contact sensor 63 is shown in FIGS. 6A-6B as extending outward from a distal end 364 of upper member 361 (column arm 361), it should be understood that contact sensor 63 may extend from any portion of upper member 361 (column arm 361).

4. Microprocessor(s)

Microprocessor 18 may be remotely located relative to the other components of exemplary chromatography system 100 or may be directly connected to one or more components within exemplary chromatography system 100. Microprocessor 18 is programmed to (i) recognize signals from various components within exemplary chromatography system 100 (e.g., machine readable tag readers, tray sensors, and/or cartridge height sensing device signals) and (ii) initiate one or more signal-specific automated steps in response to receiving one or more signals (e.g., reading existing data from a tag, writing new data onto a tag, changing one or more process settings, routing a given fraction to a specific fraction vessel along a fraction collection tray, starting or stopping a given process, etc.). As long as microprocessor 18 is capable of (i) recognizing signals from various components within exemplary chromatography system 100, and (ii) initiate one or more signal-specific automated steps in response to receiving one or more signals, microprocessor 18 may be in any location relative to exemplary chromatography system 100.

Although not shown in exemplary chromatography system 100, it should be understood that exemplary chromatography system 100 comprises one or more user interface stations (e.g., a personal computer, laptop, touch screen, keyboard, etc.), as needed, to enable a user to safely operate exemplary chromatography system 100.

B. Chromatography System Configurations

The chromatography systems of the present invention may comprise one or more of the above-described individual system components. For example, in one embodiment, the chromatography system comprises (i) the above-described fraction collection system comprising at least two stationary machine readable tag readers and at least two tray sensors in combination with (ii) at least one of the above-described mobile machine readable tag readers. In some embodiments, the mobile machine readable tag reader is operatively adapted to write new data onto one or more machine readable tags.

Regardless of the configuration, the chromatography systems of the present invention utilize one or more components (e.g., machine readable tags and readers/writers, optical sensors, and electronic sensors) to collect and monitor critical operational functions within a given chromatography system, and act intelligently with the information to ensure safe and intuitive operations.

In one desired configuration, the chromatography system of the present invention comprises three strategically placed machine readable tag readers/writers, namely, one mobile machine readable tag reader (e.g., RFID reader/writer such as mobile machine readable tag reader 30) on cartridge support member 36 as shown in FIG. 3, and two stationary machine readable tag readers (e.g., RFID reader/writer such as stationary machine readable tag readers 43) mounted along back bay wall surface 42 of a fraction collection tray bay 40 as shown in FIG. 4. The three strategically placed machine readable tag readers/writers are positioned to minimize read/write distance and ensure read/write accuracy. The chromatography system also comprises optical tray sensors 41 mounted along back bay wall surface 42 of a fraction collection tray bay 40 as shown in FIG. 4. The chromatography system further comprises cartridge height sensing device 60 as shown in FIGS. 6A-6B.

II Methods of Making Chromatography Systems and System Components

The present invention is further directed to methods of making chromatography systems comprising one or more of the above-described system components. In one exemplary method, the method of making a chromatography system comprises incorporating a mobile or stationary machine readable tag reader (e.g., mobile machine readable tag reader 30 or stationary machine readable tag reader 43) into the chromatography system, wherein the mobile or stationary machine readable tag reader is operatively adapted to (i) read existing tag data from a machine readable tag; and (ii) write new data onto the machine readable tag. The method may further comprise incorporating (i) one or more chromatography cartridges, (ii) one or more fraction collector trays, or (iii) both (i) to (ii) into the chromatography system, wherein each chromatography cartridge and/or fraction collector tray comprises at least one machine readable tag (typically one) thereon.

Methods of making a chromatography system may also comprise incorporating a fraction collection system into the chromatography system, wherein the fraction collection system comprises a fraction collector tray bay (e.g., fraction collector tray bay 40); and one or more sensors (e.g., one or more optical sensors 41) positioned along one or more bay wall surfaces (e.g., bay wall surface 42) of the fraction collector tray bay, the one or more sensors being operatively adapted to detect one or more fraction collector trays (e.g., fraction collector trays 50) positioned within the fraction collector tray bay. The exemplary method may further comprise incorporating into the chromatography system one or more stationary machine readable tag readers (e.g., stationary machine readable tag readers 43) positioned along the one or more bay wall surfaces (e.g., bay wall surface 42) of the fraction collector tray bay, wherein each of the one or more stationary machine readable tag readers is operatively adapted to read existing tag data from a machine readable tag on a tray surface of a fraction collector tray (e.g., tray tag 51). The exemplary method may even further comprise incorporating into the chromatography system one or more fraction collector trays (e.g., fraction collector trays 50) configured to be positioned within the fraction collector tray bay, wherein each of the one or more fraction collector trays comprises at least one machine readable tag (typically, a single tag) positioned along a tray surface of the fraction collector tray.

In one exemplary method, the method of making a chromatography system comprises (1) incorporating a fraction collection system into the chromatography system, wherein the fraction collection system comprises (i) a fraction collector tray bay (e.g., fraction collector tray bay 40); (ii) one or more sensors (e.g., optical sensors 41) positioned along one or more bay wall surfaces (e.g., bay wall surface 42) of the fraction collector tray bay, the one or more sensors being operatively adapted to detect one or more fraction collector trays (e.g., fraction collector trays 50) positioned within the fraction collector tray bay; (iii) one or more stationary machine readable tag readers (e.g., stationary machine readable tag readers 43) positioned along the one or more bay wall surfaces (e.g., bay wall surface 42) of the fraction collector tray bay, each of the one or more stationary machine readable tag readers being operatively adapted to read existing tag data from a machine readable tag on a surface of a fraction collector tray (e.g., tray tag 51); and (iv) one or more fraction collector trays (e.g., fraction collector trays 50) configured to be positioned within the fraction collector tray bay, wherein each of the one or more fraction collector trays comprises at least one machine readable tag (typically, a single tag) positioned along a tray surface of the fraction collector tray (e.g., tray tag 51); (2) incorporating at least one mobile machine readable tag reader (e.g., mobile machine readable tag reader 30) into the chromatography system, wherein each mobile machine readable tag reader is operatively adapted to read existing tag data from a machine readable tag on a surface of a chromatography cartridge (e.g., machine readable tag 32); and (3) incorporating at least one chromatography cartridge (e.g., cartridge 31) into the chromatography system, wherein each chromatography cartridge has at least one machine readable tag (typically, a single tag) positioned along a surface of the chromatography cartridge (e.g., machine readable tag 32). Desirably, one or more (or each) of the machine readable tag readers of the resulting chromatography system (e.g., stationary machine readable tag readers 43 and mobile machine readable tag reader 30) is operatively adapted to write new tag data onto one or more machine readable tags within the chromatography system (e.g., machine readable tag 32 and/or tray tag 51).

The present invention is further directed to methods of making system components within a chromatography system. In one exemplary embodiment, the method of making a system component comprises incorporating one or more sensors (e.g., one or more optical sensors 41) into a fraction collection system. The method may comprise positioning one or more sensors (e.g., one or more optical sensors) along one or more bay wall surfaces (e.g., bay wall surface 42) of a fraction collector tray bay (e.g., fraction collector tray bay 40), the one or more sensors being operatively adapted to detect one or more fraction collector trays (e.g., fraction collector trays 50) positioned within the fraction collector tray bay. The method may further comprise positioning one or more stationary machine readable tag readers (e.g., stationary machine readable tag readers 43) along the one or more bay wall surfaces (e.g., bay wall surface 42) of the fraction collector tray bay (e.g., fraction collector tray bay 40), wherein each of the one or more stationary machine readable tag readers is operatively adapted to read existing tag data from a machine readable tag on a tray surface of a fraction collector tray (e.g., tray tag 51). The method may even further comprise forming one or more fraction collector trays (e.g., fraction collector trays 50) configured to be positioned within the fraction collector tray bay (e.g., fraction collector tray bay 40), wherein each of the one or more fraction collector trays comprises at least one machine readable tag (typically, a single tag) positioned along a tray surface of the fraction collector tray (e.g., tray tag 51).

In another exemplary embodiment, the method of making a system component comprises positioning one or more stationary machine readable tag readers (e.g., stationary machine readable tag readers 43) along one or more bay wall surfaces (e.g., bay wall surface 42) of a fraction collector tray bay (e.g., fraction collector tray bay 40), wherein each of the one or more stationary machine readable tag readers is operatively adapted to read existing tag data from a machine readable tag on a tray surface of a fraction collector tray (e.g., tray tag 51); and forming one or more fraction collector trays (e.g., fraction collector trays 50) configured to be positioned within the fraction collector tray bay, wherein each of the one or more fraction collector trays comprises a single machine readable tag positioned along a tray surface of the fraction collector tray (e.g., tray tag 51). In some embodiments, the step of forming one or more fraction collector trays comprises forming fraction collector trays configured to be positioned in a side-by-side arrangement within the fraction collector tray bay so that an outer perimeter of at least two side-by-side fraction collector trays each independently abut two adjacent bay side wall surfaces when positioned within the fraction collector tray bay.

III. Methods of Using Chromatography Systems and System Components Within Chromatography Systems The present invention is even further directed to methods of using chromatography systems and system components within a chromatography system. The method of using a system component may comprise reading existing tag data from a machine readable tag within a chromatography system via a mobile or stationary machine readable tag reader (e.g., mobile machine readable tag reader 30 or stationary machine readable tag reader 43); and writing new data onto the machine readable tag within the chromatography system via the mobile or stationary machine readable tag reader (e.g., mobile machine readable tag reader 30 or stationary machine readable tag reader 43).

Some methods of using a system component may comprise utilizing one or more sensors (e.g., one or more optical sensors 41) to detect one or more fraction collector trays (e.g., fraction collector trays 50) positioned within a fraction collector tray bay (e.g., fraction collector tray bay 40) of a fraction collection system within a chromatography system. The one or more sensors may be positioned along one or more bay wall surfaces (e.g., bay wall surface 42) of the fraction collector tray bay (e.g., fraction collector tray bay 40) so as to detect the presence or absence of one or more fraction collector trays (e.g., fraction collector trays 50) positioned within the fraction collector tray bay.

Methods of using a system component may further comprise utilizing one or more stationary machine readable tag readers (e.g., stationary machine readable tag reader 43) positioned along one or more bay wall surfaces (e.g., bay wall surface 42) of a fraction collector tray bay (e.g., fraction collector tray bay 40) to read existing tag data from a machine readable tag (and, if desired, write new data onto the tag) on a tray surface of a fraction collector tray (e.g., tray tag 51).

Other methods of using a system component comprise utilizing one or more stationary machine readable tag readers (e.g., stationary machine readable tag reader 43) positioned along one or more bay wall surfaces (e.g., bay wall surface 42) of a fraction collector tray bay (e.g., fraction collector tray bay 40) to read existing tag data from a machine readable tag (and, if desired, write new data onto the tag) on a tray surface of a fraction collector tray (e.g., tray tag 51); and collecting one or more sample fractions within one or more collection vessels positioned at one or more specific locations along the fraction collector tray (e.g., fraction collector tray 50) based on the existing tag data (e.g., existing tag data on tray tag 51). Typically, each fraction collector tray (e.g., fraction collector tray 50) within the chromatography system comprises a single machine readable tag (e.g., tray tag 51) positioned along an abutting tray surface (i.e., a tray surface (e.g., tray surface 52) that abuts a bay wall surface of the fraction collector tray bay (e.g., bay wall surface 42)) of a given fraction collector tray.

In some embodiments, the method of using a system component may comprise utilizing one or more system components in a chromatography system, wherein the method comprises utilizing at least one mobile machine readable tag reader (e.g., mobile machine readable tag reader 30) in combination with at least one stationary machine readable tag reader (e.g., stationary machine readable tag reader 43) within the chromatography system, wherein each machine readable tag reader is operatively adapted to read existing tag data from a machine readable tag, and at least one (or each) of the machine readable tag readers is also operatively adapted to write new tag data onto a given machine readable tag within the chromatography system. The exemplary methods may further comprise utilizing one or more machine readable tags within the chromatography system either alone or in combination with (i) one or more chromatography cartridges, (ii) one or more fraction collector tray bays, or both (i) and (ii).

As discussed above, the system components of the present invention enable efficient, safe and intelligent operation of a given chromatography system. For example, swappable, extendable fraction collector trays allow a user to extend fraction collection capabilities without purchasing additional fraction collectors. Information collected from one or more optical sensors 41 informs a given system that a fraction collector tray (e.g., fraction collector tray 50) is installed, while machine readable tray tag 51 (e.g., an RFID inlay) informs the system of the type of tray and its unique identifier.

The system components may provide that all trays (e.g., fraction collector trays 50) have a unique identifier that distinguishes one tray from another. In this exemplary embodiment, the system will know when a new tray has been placed into the system. If a tray is removed during a run and a new tray of the same size or a different size is installed, the system will give a user the option to extend the fraction collector capabilities or replace a given tray. The user will have the option to continue or extend the fraction collection capabilities to as many trays as needed.

The system components also enable pull and pause fraction collector sampling. Users periodically need to take samples from a fraction collector vial during a run. If a user pulls a tray (e.g., fraction collector tray 50) while the system of the present invention is running, a tray bay sensor (e.g., optical sensors 41) will trigger the system to pause and wait to restart once the tray bay sensor (e.g., optical sensors 41) identifies that the tray (e.g., fraction collector tray 50) has been reinstalled. If the system identifies that machine readable tray tag 51 of the tray (e.g., the RFID unique identifier) has not changed, the system will resume where it left off. If the machine readable tray tag 51 of the tray (e.g., the RFID unique identifier) has changed, the user will be prompted regarding the change, and how to restart collecting if the user wishes to continue the collection process.

The system components further enable mix and match fraction collector trays and collection patterns. A user may use two different vial size fraction collector trays in the system at any time and collect peak, non-peaks in two different trays during a run. The machine readable tray tag 51 of the tray (e.g., the RFID unique identifier) on each tray is embedded with a unique ID, vial size and pattern. The collection pattern and volume is dependent on the information collected from the machine readable tray tag 51 of a given tray (e.g., the RFID unique identifier). Since the system knows the flow rate, time for each collected peak and non-peak, vial size, position and maximum volume for each vial, the system is able to collect peaks in one tray and non-peaks in another. This allows the user to collect any and all peaks in any vial pattern and size in a single run.

EXAMPLES

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

A 12 g Reveleris silica cartridge, equipped with an RFID tag, is installed on a Reveleris flash chromatography system. The RFID reader on the Reveleris system reads the tag on the silica cartridge that contains the column size, packing type and number of times the cartridge has been used. Based on the column size, the Reveleris sets the default flow to 25 ml/minute and the system upper pressure limit to 200 psig. A sample is analyzed and thereafter the flash system's RFID reader writes to the RFID tag on the cartridge incrementing the number of times the cartridge has been used by one.

While the invention has been described with a limited number of embodiments, these specific embodiments are not intended to limit the scope of the invention as otherwise described and claimed herein. It may be evident to those of ordinary skill in the art upon review of the exemplary embodiments herein that further modifications, equivalents, and variations are possible. All parts and percentages in the examples, as well as in the remainder of the specification, are by weight unless otherwise specified. Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit, $R_L$, and an upper limit $R_U$, is disclosed, any number R falling within the range is specifically disclosed. In particular, the following numbers R within the range are specifically disclosed: $R=R_L+k(R_U-R_L)$, where k is a variable ranging from 1% to 100% with a 1% increment, e.g., k is 1%, 2%, 3%, 4%, 5% ... 50%, 51%, 52% ... 95%, 96%, 97%, 98%, 99%, or 100%. Moreover, any numerical range represented by any two values of R, as calculated above is also specifically disclosed. Any modifications of the invention, in addition to those shown and described herein, will become apparent to those skilled in the art from the foregoing description and accompanying drawings. Such modifications are intended to fall within the scope of the appended claims. All publications cited herein are incorporated by reference in their entirety.

What is claimed is:

1. A chromatography system comprising:
    a machine readable tag reader being constructed to enable movement of a tag reader component along different axes relative to a machine readable tag, said machine readable tag reader being operatively adapted to: (a) read existing tag data from a machine readable tag; (b) write new data onto the machine readable tag; and (c) move relative to the machine readable tag;
    a chromatography cartridge comprising an outer cartridge surface and a machine readable tag along said outer cartridge surface; and
    a fraction collector tray comprising an outer tray surface and a machine readable tag along said outer tray surface.

2. The chromatography system of claim 1, wherein the new data comprises historical cartridge use data of said chromatography cartridge, said historical cartridge use data comprising one or more pieces of data including a date of cartridge use, a solvent used in the cartridge on the date, a count of how many times the cartridge has been used, sample type, user name, and any combination thereof.

3. The chromatography system of claim 1, wherein the existing tag data comprises data that sets one or more operational conditions of the chromatography system.

4. The chromatography system of claim 1, wherein said machine readable tag reader comprises:
   (a) a reader arm having a first end and a second end, said first end being connectable to an object within the chromatography system, and said second end being operatively adapted to move relative to the object when said first end is connected to the object; and
   (b) a tag reader component attached to said second end, wherein said tag reader component is operatively adapted to (i) read existing tag data from at least one of said one or more machine readable tags, (ii) write new data onto at least one of said one or more machine readable tags, and (iii) move relative to said second end.

5. The chromatography system of claim 1, wherein said chromatography cartridge further comprises solid phase material within said chromatography cartridge.

6. The chromatography system of claim 5, wherein said solid phase material comprises silica.

7. The chromatography system of claim 1, further comprising a fraction collector tray bay, said fraction collector tray bay comprising (1) one or more sensors positioned along one or more bay wall surfaces of said fraction collector tray bay, said one or more sensors being operatively adapted to detect one or more fraction collector trays positioned within said fraction collector tray bay, and (2) one or more stationary machine readable tag readers positioned along said one or more bay wall surfaces of said fraction collector tray bay, each of said one or more stationary machine readable tag readers being operatively adapted to read existing tag data from a machine readable tag on a surface of a fraction collector tray.

8. A chromatography system comprising:
   a machine readable tag reader being constructed to enable movement of a tag reader component along different axes relative to a machine readable tag, said machine readable tag reader comprising: (a) a reader having a first end and a second end, said first end being connectable to an object within the chromatography system, and said second end being operatively adapted to move relative to the object when said first end is connected to the object; and (b) a tag reader component attached to said second end, wherein said tag reader component is operatively adapted to (i) move relative to said second end, (ii) read existing tag data from a machine readable tag, and (iii) write new data onto the machine readable tag;
   one or more chromatography cartridges; and
   a machine readable tag on each chromatography cartridge.

9. The chromatography system of claim 8, said tag reader component being operatively adapted to move so as to position an outer surface of said tag reader component adjacent to and over an outer surface of the machine readable tag.

10. The chromatography system of claim 8, wherein each chromatography cartridge of said one or more chromatography cartridges comprises solid phase material within said chromatography cartridge.

11. The chromatography system of claim 10, wherein said solid phase material comprises silica.

12. A fraction collection system of a chromatography system, said fraction collection system comprising:
   (a) a fraction collector tray bay;
   (b) one or more sensors positioned along one or more bay wall surfaces of said fraction collector tray bay, said one or more sensors being operatively adapted to detect one or more fraction collector trays positioned within said fraction collector tray bay; and
   (c) one or more stationary machine readable tag readers positioned along said one or more bay wall surfaces of said fraction collector tray bay, each of said one or more stationary machine readable tag readers being operatively adapted to read existing tag data from a machine readable tag on a surface of a fraction collector tray.

13. The fraction collection system of claim 12, wherein at least one of said one or more sensors comprises an optical sensor.

14. The fraction collection system of claim 12, wherein at least one of said one or more stationary machine readable tag readers is operatively adapted to (ii) write new data onto a given machine readable tag.

15. The fraction collection system of claim 12, further comprising:
   one or more fraction collector trays configured to be positioned within said fraction collector tray bay, wherein each of said one or more fraction collector trays comprises a machine readable tag positioned along a tray surface of the fraction collector tray.

16. The fraction collection system of claim 15, wherein each of said one or more fraction collector trays comprises a single machine readable tag positioned along a tray surface of the fraction collector tray.

17. The fraction collection system of claim 16, wherein said single machine readable tag comprises fraction data, said fraction data comprising (i) fraction vessel positions along an outer tray surface of the fraction collector tray, (ii) empty fraction vessel positions along the outer tray surface of the fraction collector tray, (iii) occupied fraction vessel positions along the outer tray surface of the fraction collector tray, (iv) fraction vessel information for each fraction vessel positioned within one or more of the occupied fraction vessel positions, (v) fraction information for each fraction positioned within one or more of the occupied fraction vessel positions, or (vi) any combination of (i) to (v).

18. The fraction collection system of claim 15, wherein at least two fraction collector trays are positioned side-by-side relative to one another, and an outer perimeter of said at least two side-by-side fraction collection trays faces at least two adjacent bay wall surfaces of said fraction collector tray bay.

19. The fraction collection system of claim 18, wherein said one or more bay wall surfaces comprise a stationary machine readable tag reader for each fraction collector tray positioned within the fraction collector tray bay.

20. The fraction collection system of claim 18, wherein a single bay wall surface comprises at least two stationary machine readable tag readers for said at least two side-by-side fraction collector trays.

21. The fraction collection system of claim 12, further comprising:
   a mobile machine readable tag reader, said mobile machine readable tag reader comprising a reader arm having a first end and a second end, said first end being connectable to an object within the chromatography system, and said second end being operatively adapted to move relative to the object when said first end is connected to the object; and a tag reader component attached to said second end, wherein said tag reader component is operatively adapted to (i) move relative to said second end, and (ii) read existing tag data from a machine readable tag.

22. The fraction collection system of claim 21, wherein said tag reader component is operatively adapted to (iii) write new data onto the machine readable tag.

23. A chromatography system comprising the fraction collection system of claim 21.

24. A chromatography system comprising the fraction collection system of claim 12.

25. A chromatography system comprising the fraction collection system of claim 12.

26. A chromatography system comprising:
a mobile machine readable tag reader, said mobile machine readable tag reader being operatively adapted to (i) write new data onto a machine readable tag, and (ii) move relative to the machine readable tag;
at least one chromatography cartridge comprising (i) an outer cartridge surface, (ii) a machine readable tag positioned along said outer cartridge surface, and (iii) solid phase material within said chromatography cartridge;
a fraction collector tray bay (i) comprising one or more bay wall surfaces, and (ii) sized to house two or more fraction collector trays; and
one or more stationary machine readable tag readers positioned along said one or more bay wall surfaces of said fraction collector tray bay, each of said one or more stationary machine readable tag readers being operatively adapted to read existing tag data from a machine readable tag on a surface of a given fraction collector tray.

27. The chromatography system of claim 26, further comprising one or more fraction collector trays configured to be positionable within said fraction collector tray bay, wherein each of said one or more fraction collector trays comprises a machine readable tag positioned along a tray surface of the fraction collector tray.

28. The chromatography system of claim 26, further comprising one or more optical sensors positioned along said one or more bay wall surfaces of said fraction collector tray bay, said one or more optical sensors being operatively adapted to detect one or more fraction collector trays positioned within said fraction collector tray bay.

* * * * *